(12) United States Patent
Abebe et al.

(10) Patent No.: US 8,535,715 B2
(45) Date of Patent: Sep. 17, 2013

(54) BILAYER TABLET FORMULATIONS

(75) Inventors: Admassu Abebe, Princeton, NJ (US); Kyle Martin, Princeton, NJ (US); Jatin M. Patel, Princeton, NJ (US); Divyakant Desai, Princeton, NJ (US); Peter Timmins, Wirral (GB)

(73) Assignees: Bristol-Myers Squibb Company, Princeton, NJ (US); AstraZeneca UK Limited, London (GB)

( * ) Notice: Subject to any disclaimer, the term of this patent is extended or adjusted under 35 U.S.C. 154(b) by 0 days.

(21) Appl. No.: 13/509,210

(22) PCT Filed: Nov. 12, 2010

(86) PCT No.: PCT/US2010/056529
§ 371 (c)(1),
(2), (4) Date: Jul. 25, 2012

(87) PCT Pub. No.: WO2011/060256
PCT Pub. Date: May 19, 2011

(65) Prior Publication Data
US 2012/0282336 A1    Nov. 8, 2012

Related U.S. Application Data

(60) Provisional application No. 61/261,087, filed on Nov. 13, 2009.

(51) Int. Cl.
| | | |
|---|---|---|
| A61K 9/24 | (2006.01) |
| A61P 3/10 | (2006.01) |
| A61P 3/06 | (2006.01) |
| A61P 27/12 | (2006.01) |
| A61P 27/02 | (2006.01) |
| A61P 13/12 | (2006.01) |
| A61P 25/00 | (2006.01) |
| A61P 3/04 | (2006.01) |
| A61P 17/02 | (2006.01) |
| A61P 9/10 | (2006.01) |
| A61P 9/12 | (2006.01) |
| A61K 31/155 | (2006.01) |
| A61K 31/7034 | (2006.01) |
| A61K 38/28 | (2006.01) |
| A61K 38/26 | (2006.01) |

(52) U.S. Cl.
USPC ........... 424/465; 424/472; 424/471; 514/635; 514/23; 514/6.5; 514/7.2

(58) Field of Classification Search
None
See application file for complete search history.

(56) References Cited

U.S. PATENT DOCUMENTS

| | | | |
|---|---|---|---|
| 5,955,106 A * | 9/1999 | Moeckel et al. | 424/464 |
| 6,117,451 A | 9/2000 | Kumar | |
| 7,214,387 B2 | 5/2007 | Sanghvi | |
| 2006/0057202 A1* | 3/2006 | Antarkar et al. | 424/472 |
| 2008/0234366 A1* | 9/2008 | Bindra et al. | 514/460 |

FOREIGN PATENT DOCUMENTS

| | | |
|---|---|---|
| WO | WO 2005/117841 A1 | 12/2005 |
| WO | WO 2008/113000 A1 | 9/2008 |
| WO | WO 2008/116179 A1 | 9/2008 |
| WO | WO 2010/045656 A2 | 4/2010 |

OTHER PUBLICATIONS

Mandal et al., Formulation and in Vitro Studies of a Fixed-Dose Combination of a Bilayer Matrix Tablet Containing Metformin HCl as Sustained Release and Gliizide as Immediate Release, Drug Development and Industrial Phamacy, 2008, vol. 34, p. 305-313.*
Anonymous: "View of NCT01002807 on 2009_10_26," ClinicalTrials.gov archive (Oct. 26, 2009), pp. 1-3, retrieved from the internet: URL:http://clinicaltrials.gov/archive/NCTO1002807/2009_10_26.

* cited by examiner

*Primary Examiner* — Daniel Sullivan
*Assistant Examiner* — Ping Cao
(74) *Attorney, Agent, or Firm* — McDonnell Boehnen Hulbert & Berghoff LLP

(57) ABSTRACT

The present invention relates to bilayer tablet formulations comprising metformin extended release (XR) or reduced mass metformin XR formulation as the first layer, an SGLT2 inhibitor formulation as the second layer, and optionally a film coating. The present invention provides methods of preparing the bilayer tablet formulations and methods of treating diseases or disorders associated with SGLT2 activity employing the bilayer tablet formulations.

38 Claims, No Drawings

BILAYER TABLET FORMULATIONS

CROSS REFERENCE TO RELATED APPLICATIONS

This application is a national stage filing under 35 U.S.C. §371 of International Patent Application no. PCT/US10/56259, which claims the priority of U.S. Provisional Patent Application No. 61/261,087.

FIELD OF THE INVENTION

The present invention relates to bilayer tablet formulations comprising metformin extended release (XR) formulations or reduced mass metformin XR formulations as the first layer, sodium dependent glucose transporter inhibitor (SGLT2) formulations as the second layer, and optionally a film coating. The present invention provides methods of preparing the bilayer tablet formulations and methods of treating diseases or disorders associated with SGLT2 activity employing the bilayer tablet formulations.

BACKGROUND OF THE INVENTION

Type II diabetes is the most common form of diabetes accounting for 90% of diabetes cases. Over 100 million people worldwide have type-2 diabetes (nearly 17 million in the U.S.) and the prevalence is increasing dramatically in both the developed and developing worlds. Type-II diabetes is a lifelong illness, which generally starts in middle age or later part of life, but can start at any age. Patients with type-2 diabetes do not respond properly to insulin, the hormone that normally allows the body to convert blood glucose into energy or store it in cells to be used later. The problem in type-2 diabetes is a condition called insulin resistance where the body produces insulin, in normal or even high amounts, but certain mechanisms prevent insulin from moving glucose into cells. Because the body does not use insulin properly, glucose rises to unsafe levels in the blood, the condition known as hyperglycemia.

Over time, sustained hyperglycemia leads to glucotoxicity, which worsens insulin resistance and contributes to dysfunction in the beta cells of the pancreas. The degree of sustained hyperglycemia is directly related to diabetic microvascular complications and may also contribute to macrovascular complications. In this way, hyperglycemia perpetuates a cycle of deleterious effects that exacerbate type 2 diabetes control and complications.

It is now widely accepted that glycemic control makes a difference in type II diabetes patients. The goal of diabetes therapy today is to achieve and maintain as near normal glycemia as possible to prevent the long-term microvascular and macrovascular complications associated with elevated glucose in the blood. Oral therapeutic options for the treatment of type II diabetes mellitus include compounds known as: sulfonylureas, biguanides (metformin), thiazolidinediones, and alpha-glucosidase inhibitors. The active agents from each class are generally administered to patients alone. However, once monotherapy becomes inadequate, combination therapy is an attactive and rational course of action for treating hyperglycemia despite the known side effect of weight gain associated with sulfonylurea and thiazolidinone therapies.

Recently, a new class of anti-diabetics was discovered known as sodium-glucose transporter-2 inhibitors (SGLT2). SGLT2 inhibitors prevent the reabsorption of glucose into blood by the kidney. The kidney continuously filters glucose through the glomerulus into the bladder, however, nearly all of this glucose is reabsorbed. SGLT2 is the protein responsible for the majority of glucose reabsorption and helps the body retain glucose for its energy requirements. For patients with diabetes, retention of excess glucose by this pathway contributes to persistent hyperglycemia. Suppressing the activity of SGLT2 inhibits renal-glucose reabsorption in the body, thereby leading to the excretion of glucose in the urine.

Accordingly, the present invention provides bilayer tablet formulations that consist of metformin and an SGLT2 inhibitor for oral administration in the treatment of diseases or disorders associated with SGLT2 activity without weight gain associated with other therapies. The first layer of the bilayer tablet is metformin extended release (XR) or metformin XR in a reduced mass formulation. The second layer is an SGLT2 inhibitor formulation. The metformin/SGLT2 bilayer tablet of the present invention provides an antidiabetic therapy to patients that is both convenient and effective for controlling blood glucose levels.

SUMMARY OF THE INVENTION

The present invention provides bilayer tablets comprising (1) a metformin XR formulation or a reduced mass metformin XR formulation as the first layer, (2) an SGLT2 inhibitor formulation as the second layer, and (3) optionally a film coating that covers both layers. Metformin may be in the form of a pharmaceutically acceptable salt where metformin hydrochloride (HCl) is preferred. A preferred SGLT2 inhibitor is dapagliflozin or a pharmaceutically acceptable salt thereof, dapagliflozin (S) propylene glycol hydrate (1:1:1), or dapagliflozin (R) propylene glycol hydrate (1:1:1). The most preferred SGLT2 inhibitor is dapagliflozin or dapagliflozin (S) propylene glycol hydrate (1:1:1). The SGLT2 inhibitor formulation is an immediate release or an extended release formulation, where an immediate release formulation is preferred.

The metformin XR layer (1000 mg) comprises metformin, a binder, a release modifier, a lubricant, and optionally a glidant. A preferred binder is sodium carboxymethyl cellulose. Hydroxypropyl methylcellulose 2208 is a preferred release modifier. Magnesium stearate is a preferred lubricant and silicon dioxide or colloidal silicon dioxide are preferred glidants. The SGLT2 inhibitor layer comprises an SGLT2 inhibitor, two or three fillers, a disintegrant, a glidant, and a lubricant. The preferred fillers are lactose anhydrous, microcrystalline cellulose 302, pregelatinized starch, and mannitol. A preferred disintegrant is crospovidone. Silicon dioxide is the preferred glidant and magnesium stearate is the preferred lubricant. Hydroxypropyl cellulose EXF is the preferred binder.

The metformin XR layer (500 mg) comprises metformin, a binder, at least one release modifier, a filler, a lubricant, and optionally a glidant. A preferred binder is sodium carboxymethyl cellulose. The preferred release modifiers are hydroxypropyl methylcellulose 2208 in combination with hydroxypropyl methylcellulose 2910. Microcrystalline cellulose is a preferred filler. Magnesium stearate is a preferred lubricant and silicon dioxide or colloidal silicon dioxide are preferred glidants. The SGLT2 inhibitor layer comprises an SGLT2 inhibitor, two or three fillers, a disintegrant, a glidant, and a lubricant. The preferred fillers are lactose anhydrous, microcrystalline cellulose 302, pregelatinized starch, and mannitol. A preferred disintegrant is crospovidone. Silicon dioxide is the preferred glidant and magnesium stearate is the preferred lubricant. Hydroxypropyl cellulose EXF is the preferred binder.

In another aspect, the present invention provides methods of treating diseases or disorders associated with SGLT2 activity comprising administering to a mammal in need of such treatment a therapeutically effective amount of a bilayer tablet comprised of metformin XR or reduced mass metformin XR, an SGLT2 inhibitor, and optionally a film coating. The bilayer tablet formulations of the present invention can be administered to mammals, preferably humans, for the treatment of a variety of conditions and disorders associated with SGLT2 activity including, but not limited to, treating or delaying the progression or onset of diabetes (including Type I and Type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension. The formulations of the present invention can also be utilized to increase the blood levels of high density lipoprotein (HDL). In addition, the conditions, diseases, and maladies collectively referenced to as "Syndrome X" or Metabolic Syndrome as detailed in Johannsson, *J. Clin. Endocrinol. Metab.*, 82, 727-34 (1997), can be treated employing the formulations of the present invention.

In another aspect, the present invention provides methods for preparing a bilayer tablet comprising metformin XR or reduced mass metformin XR, an SGLT2 inhibitor, and optionally a film coating.

DETAILED DESCRIPTION OF THE INVENTION

Preparing bilayer tablets with significantly different weight ratios between the two layers can lead to cracking at the layer interface, separation of the layers, or even cross-contamination of the two layers. The large difference in weight ratio between the metformin and the SGLT2 inhibitor layers of Examples 4-15 provides challenges with regard to maintaining potency and content uniformity of the lower weight layer, the SGLT2 inhibitor layer. Furthermore it was found that a number of trial formulations showed cracking in the SGLT2 layers at the tablet surface in an area adjacent to but separate from the interface between the layers and parallel to that interface. Formulations of the SGLT2 layer with increased microcrystalline cellulose levels, for example, reduced or eliminated cracking, separation, and cross-contamination of the two layers while maintaining potency and uniformity of the second layer. Further, pregelatinized starch, hydroxypropyl cellulose EXF, or mannitol, can be used as a substitute for a portion of the microcrystalline cellulose. Finally, a total weight of about 300 mgs to about 400 mgs for the second layer contributed to reducing or eliminating cracking, separation, and cross-contamination of the two layers. The preferred weight of the second layer is 300 mgs. Accordingly, the present invention provides bilayer tablet formulations that reduce or eliminate cracking, separation, and cross-contamination of the metformin and SGLT2 layers and maintains or improves the SGLT2 layer potency and uniformity.

The present invention provides a bilayer tablet comprising metformin XR (1000 mg) formulations, SGLT2 inhibitor (2.5, 5.0, or 10.0 mgs) formulations, and optionally a film coating. The metformin XR formulation comprises metformin hydrochloride (HCl), sodium carboxymethyl cellulose, hydroxypropyl methylcellulose, and magnesium stearate. The SGLT2 inhibitor formulation comprises an SGLT2 inhibitor, lactose anhydrous, microcrystalline cellulose, crospovidone, silicon dioxide, and magnesium stearate. For the second layer, pregelatinized starch, hydroxypropyl cellulose EXF, or mannitol (pearlitol SD 200) can be used to substitute a portion of the microcrystalline cellulose. In addition, the second layer has a total weight of about 300 mgs to about 400 mgs. The preferred weight of the second layer is 300 mgs. The optional film coating can be Opadry® II. In a preferred embodiment, the SGLT2 inhibitor is dapagliflozin, dapagliflozin (S) PGS, or dapagliflozin (R) PGS.

In another aspect, the present invention provides a bilayer tablet wherein the metformin XR (1000 mg) formulation comprises about 50-87% metformin hydrochloride (HCl), about 1-10% sodium carboxymethyl cellulose, about 10-40% hydroxypropyl methylcellulose, about 0.1-75% magnesium stearate, and about 0-2% silicon dioxide or about 0-1.5% colloidal silicon dioxide. The SGLT2 inhibitor formulation comprises about 0.1-10% SGLT2 inhibitor, about 5-30% lactose anhydrous, about 40-90% microcrystalline cellulose, about 0-25% pregelatinized starch, about 0-20% hydroxypropyl cellulose, about 0-25% mannitol, about 1-10% crospovidone, about 0.1-5% silicon dioxide, and about 0.1-5% magnesium stearate. The optional film coating can be Opadry® II. In a preferred embodiment, the SGLT2 inhibitor is dapagliflozin or dapagliflozin (S) PGS.

In another aspect, the present invention provides a bilayer tablet wherein the metformin XR (1000 mg) formulation comprises about 64-82% metformin hydrochloride (HCl), about 3-5% sodium carboxymethyl cellulose, about 15-30% hydroxypropyl methylcellulose, about 0.1-75% magnesium stearate, and about 0-2% silicon dioxide or about 0-1.5% colloidal silicon dioxide. The SGLT2 inhibitor formulation comprises about 0.5-4% SGLT2 inhibitor, about 14-18% lactose anhydrous, about 50-80% microcrystalline cellulose, about 0-20% pregelatinized starch, about 0-15% hydroxypropyl cellulose, about 0-20% mannitol, about 2-6% crospovidone, about 0.5-2.5% silicon dioxide, and about 0.49-2% magnesium stearate. The optional film coating can be Opadry® II. In a preferred embodiment, the SGLT2 inhibitor is dapagliflozin or dapagliflozin (S) PGS.

In another aspect, the present invention provides a bilayer tablet wherein the metformin XR (1000 mg) formulation comprises about 67-71% metformin hydrochloride (HCl), about 3-5% sodium carboxymethyl cellulose, about 25-29% hydroxypropyl methylcellulose 2208, and about 0.1-0.75% magnesium stearate. The SGLT2 inhibitor formulation comprises about 0.5-4% dapagliflozin or dapagliflozin (S) PGS, about 14-18% lactose anhydrous, about 72-80% microcrystalline cellulose 302, about 2-6% crospovidone, about 0.5-2.5% silicon dioxide, and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 67-71% metformin hydrochloride (HCl), about 3-5% sodium carboxymethyl cellulose, about 25-29% hydroxypropyl methylcellulose 2208, and about 0.1-0.75% magnesium stearate. The SGLT2 inhibitor formulation comprises about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs.

In another aspect, the present invention provides a bilayer tablet wherein the metformin XR (1000 mg) formulation comprises about 67-71% metformin hydrochloride (HCl), about 3-5% sodium carboxymethyl cellulose, about 25-29% hydroxypropyl methylcellulose 2208, and about 0.1-0.75% magnesium stearate. The SGLT2 inhibitor formulation comprises about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs.

In another aspect, the present invention provides a bilayer tablet wherein the metformin XR (1000 mg) formulation comprises about 67-71% metformin hydrochloride (HCl), about 3-5% sodium carboxymethyl cellulose, about 25-29% hydroxypropyl methylcellulose 2208, and about 0.1-0.75% magnesium stearate. The SGLT2 inhibitor formulation comprises about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 0.5-4% dapagliflozin (S) PGS, about 16% lactose anhydrous, about 57-77% microcrystalline cellulose 302, about 0-19% pegelatinized starch, 0-10% hydroxypropyl cellulose EXF, about 0-15% mannitol, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 0.8% dapagliflozin or dapagliflozin (S) propylene glycol hydrate; about 16% lactose anhydrous; about 77% microcrystalline cellulose 302; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 3.4% dapagliflozin or dapagliflozin (S) propylene glycol hydrate; about 16% lactose anhydrous; about 74% microcrystalline cellulose 302; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet formulation wherein the metformin XR (1000 mg) formulation comprises about 67-73% metformin hydrochloride (HCl), about 3-5% sodium carboxymethyl cellulose, about 25-30% hydroxypropyl methylcellulose 2208, and about 0.08-0.2% magnesium stearate. The SGLT2 inhibitor formulation comprises about 0.5-4% dapagliflozin (S) PGS, about 14-18% lactose anhydrous, about 55-70% microcrystalline cellulose 302, about 10-25% pregelatinized starch, about 3-5% crospovidone, about 0.5-2.5% silicon dioxide, and about 0.5-2% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin (S) PGS, about 16% lactose anhydrous, about 56-64% microcrystalline cellulose 302, about 13-19% pregelatinized starch, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet formulation wherein the metformin XR (1000 mg) formulation comprises about 67-73% metformin hydrochloride (HCl), about 3-5% sodium carboxymethyl cellulose, about 25-30% hydroxypropyl methylcellulose 2208, and about 0.08-0.2% magnesium stearate. The SGLT2 inhibitor formulation comprises about 0.5-4% dapagliflozin (S) PGS, about 14-18% lactose anhydrous, about 55-70% microcrystalline cellulose 302, about 5-20% hydroxypropyl Cellulose EXF, about 3-5% crospovidone, about 0.5-2.5% silicon dioxide, and about 0.5-2% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin (S) PGS, about 16% lactose anhydrous, about 66% microcrystalline cellulose 302, about 10% hydroxypropyl cellulose EXF, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 67-73% metformin hydrochloride (HCl), about 3-5% sodium carboxymethyl cellulose, about 25-30% hydroxypropyl methylcellulose 2208, and about 0.08-0.2% magnesium stearate. The SGLT2 inhibitor formulation comprises about 0.5-4% dapagliflozin (S) PGS, about 14-18% lactose anhydrous, about 55-70% microcrystalline cellulose 302, about 5-25% mannitol, about 3-5% crospovidone, about 0.5-2.5% silicon dioxide, and about 0.5-2% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (1000 mg) formulation comprises about 69% metformin hydrochloride (HCl), about 3.5% sodium carboxymethyl cellulose, about 27% hydroxypropyl methylcellulose 2208, and about 0.49% magnesium stearate. The SGLT2 inhibitor formulation comprises about 1.7% dapagliflozin (S) PGS, about 16% lactose anhydrous, about 61% microcrystalline cellulose 302, about 15% mannitol, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

The present invention also provides a bilayer tablet comprising metformin XR (500 mg) formulations, SGLT2 inhibitor (2.5, 5.0, or 10.0 mgs) formulations, and optionally a film coating. The metformin XR formulation comprises metformin hydrochloride (HCl), sodium carboxymethyl cellulose, hydroxypropyl methylcellulose, microcrystalline cellulose, and magnesium stearate. The SGLT2 inhibitor formulation comprises an SGLT2 inhibitor, lactose anhydrous, microcrystalline cellulose, crospovidone, silicon dioxide, and magnesium stearate. For the second layer, pregelatinized starch, hydroxypropyl cellulose EXF, or mannitol (pearlitol SD 200) can be used to substitute a portion of the microcrystalline cellulose. In addition, the second layer has a total weight of about 300 mgs to about 400 mgs. The preferred weight of the second layer is 300 mgs. The optional film coating can be Opadry® II. In a preferred embodiment, the SGLT2 inhibitor is dapagliflozin, dapagliflozin (S) PGS, or dapagliflozin (R) PGS.

In another aspect, the present invention provides a bilayer tablet wherein the metformin XR (500 mg) formulation comprises about 40-60% metformin hydrochloride (HCl), about 1-10% sodium carboxymethyl cellulose, about 20-45% hydroxypropyl methylcellulose, about 5-15% microcrystalline cellulose, about 0.1-0.75% magnesium stearate, and about 0-2% silicon dioxide or about 0-1.5% colloidal silicon dioxide. The SGLT2 inhibitor formulation comprises about 0.1-10% SGLT2 inhibitor, about 5-30% lactose anhydrous, about 40-90% microcrystalline cellulose, about 0-25% pregelatinized starch, about 0-20% hydroxypropyl cellulose, about 0-25% mannitol, about 1-10% crospovidone, about 0.1-5% silicon dioxide, and about 0.1-5% magnesium stearate. The optional film coating can be Opadry® II. In a preferred embodiment, the SGLT2 inhibitor is dapagliflozin or dapagliflozin (S) PGS.

In another aspect, the present invention provides a bilayer tablet wherein the metformin XR (500 mg) formulation comprises about 42-55% metformin hydrochloride (HCl), about 4-6% sodium carboxymethyl cellulose, about 30-40% hydroxypropyl methylcellulose, about 5-15% microcrystalline cellulose, about 0.1-0.75% magnesium stearate, and about 0-2% silicon dioxide or about 0-1.5% colloidal silicon dioxide. The SGLT2 inhibitor formulation comprises about 0.5-4% SGLT2 inhibitor, about 14-18% lactose anhydrous, about 65-80% microcrystalline cellulose, about 0-20% pregelatinized starch, about 0-15% hydroxypropyl cellulose, about 0-20% mannitol, about 2-6% crospovidone, about 0.5-2.5% silicon dioxide, and about 0.49-2% magnesium stearate. The optional film coating can be Opadry® II. In a preferred embodiment, the SGLT2 inhibitor is dapagliflozin or dapagliflozin (S) PGS.

In another aspect, the present invention provides a bilayer tablet wherein the metformin XR (500 mg) formulation comprises about 46-50% metformin hydrochloride (HCl), about 4-6% sodium carboxymethyl cellulose, about 30-40% hydroxypropyl methylcellulose 2208, about 0.1-1.5% hydroxypropyl methylcellulose 2910, 5-15% microcrystalline cellulose, and about 0.1-0.75% magnesium stearate. The SGLT2 inhibitor formulation comprises about 0.5-4% dapagliflozin or dapagliflozin (S) PGS, about 14-18% lactose anhydrous, about 72-80% microcrystalline cellulose 302, about 2-6% crospovidone, about 0.5-2.5% silicon dioxide, and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (500 mg) formulation comprises about 46-50% metformin hydrochloride (HCl), about 4-6% sodium carboxymethyl cellulose, about 30-40% hydroxypropyl methylcellulose 2208, 0.1-1.5% hydroxypropyl methylcellulose 2910, 5-15% microcrystalline cellulose, and about 0.1-0.75% magnesium stearate. The SGLT2 inhibitor formulation comprises about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs.

In another aspect, the present invention provides a bilayer tablet wherein the metformin XR (500 mg) formulation comprises about 46-50% metformin hydrochloride (HCl), about 4-6% sodium carboxymethyl cellulose, about 30-40% hydroxypropyl methylcellulose 2208, 0.1-1.5% hydroxypropyl methylcellulose 2910, 5-15% microcrystalline cellulose, and about 0.1-0.75% magnesium stearate. The SGLT2 inhibitor formulation comprises about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs.

In another aspect, the present invention provides a bilayer tablet wherein the metformin XR (500 mg) formulation comprises about 46-50% metformin hydrochloride (HCl), about 4-6% sodium carboxymethyl cellulose, about 30-40% hydroxypropyl methylcellulose 2208, 0.1-1.5% hydroxypropyl methylcellulose 2910, 5-15% microcrystalline cellulose, and about 0.1-0.75% magnesium stearate. The SGLT2 inhibitor formulation comprises about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs.

In another aspect, the present invention provides a bilayer tablet wherein the metformin XR (500 mg) formulation comprises about 48-49% metformin hydrochloride (HCl), about 4.5-5% sodium carboxymethyl cellulose, about 34.5-35% hydroxypropyl methylcellulose 2208, 0.8-1.2% hydroxypropyl methylcellulose 2910, about 9.75-10.25% microcrystalline cellulose, and about 0.34% magnesium stearate. The SGLT2 inhibitor formulation comprises about 0.5-4% dapagliflozin (S) PGS, about 16% lactose anhydrous, about 72-77% microcrystalline cellulose 302, about 0-19% pegelatinized starch, 0-10% hydroxpropyl cellulose EXF, about 0-15% mannitol, about 4% crospovidone, about 0.5-1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (500 mg) formulation comprises about 48-49% metformin hydrochloride (HCl), about 4.5-5% sodium carboxymethyl cellulose, about 34.5-35% hydroxypropyl methylcellulose 2208, 0.8-1.2% hydroxypropyl methylcellulose 2910, about 9.75-10.25% microcrystalline cellulose, and about 0.34% magnesium stearate. The SGLT2 inhibitor formulation comprises about 0.5-4% dapagliflozin (S) PGS, about 16% lactose anhydrous, about 72-77% microcrystalline cellulose 302, about 4% crospovidone, about 0.5-1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

Formulations that reduce the mass of the metformin XR layer, as compared with known or currently available formulations of metformin XR, without affecting the amount of active ingredient are desirable because these formulations provide lower weight differentials between the two layers thereby reducing or eliminating problems associated with the manufacture of a bilayer tablet (cracking, separation, cross-contamination). In addition, the bilayer tablets are rendered smaller and more suitable for oral administration to patients. The present invention provides reduced mass metformin XR formulations that comprise silicon dioxide or colloidal silicon dioxide with reduced amounts of hydroxypropyl methylcellulose. Hydroxypropyl methylcellulose is reduced from about 27% to about 18%. These formulations improve compactability and reduce layer weight ratios from about 4.8:1 to about 4.4:1 while maintaining similar metformin release rates.

Accordingly, the present invention provides bilayer tablets comprising reduced mass metformin XR (1000 mgs) formulations, SGLT2 inhibitor (2.5, 5.0, 10.0 mgs) formulations, and optionally a film coating. The reduced mass metformin XR formulations comprise metformin HCl, sodium carboxymethyl cellulose, hydroxypropyl methylcellulose, silicon dioxide or colloidal silicon dioxide, and magnesium stearate. The SGLT2 inhibitor formulation comprises the SGLT2 inhibitor, lactose anhydrous, microcrystalline cellulose, crospovidone, silicon dioxide, and magnesium stearate. For the second layer, pregelatinized starch, hydroxypropyl cellulose, or mannitol can be used to substitute a portion of the microcrystalline cellulose. The total weight of the SGLT2 inhibitor layer is about 300 mgs to about 400 mgs where the preferred weight is about 300 mgs. The optional film coating can be Opadry® II. In a preferred embodiment, the SGLT2 inhibitor is dapagliflozin, dapagliflozin (S) PGS, or dapagliflozin (R) PGS.

In another aspect, the present invention provides a bilayer tablet wherein the reduced mass metformin XR (1000 mgs) formulation comprises about 70-85% metformin hydrochloride (HCl), about 2-6% sodium carboxymethyl cellulose, about 15-27% hydroxypropyl methylcellulose 2208, about 0.75-1.25% silicon dioxide or about 0.25%-0.75% colloidal silicon dioxide, and about 0.05-5% magnesium stearate. The SGLT2 inhibitor formulation comprises about 0.1-10% SGLT2 inhibitor, about 5-30% lactose anhydrous, about 40-90% microcrystalline cellulose 302, about 0-25% pregelatinized starch, about 0-20% hydroxypropyl cellulose EXF, about 0-25% mannitol (pearlitol SD 200), about 1-10% crospovidone, about 0.1-5% silicon dioxide, and about 0.1-

5% magnesium stearate. The total weight of the SGLT2 inhibitor layer is about 300 mgs to about 400 mgs where the preferred weight is about 300 mgs. The optional film coating can be Opadry® II. In a preferred embodiment, the SGLT2 inhibitor is dapagliflozin or dapagliflozin (S) PGS.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 0.1-10% SGLT2 inhibitor, about 5-30% lactose anhydrous, about 40-90% microcrystalline cellulose 302, about 0-25% pregelatinized starch, about 0-20% hydroxypropyl cellulose EXF, about 0-25% mannitol (pearlitol SD 200), about 1-10% crospovidone, about 0.1-5% silicon dioxide, and about 0.1-5% magnesium stearate. The total weight of the SGLT2 inhibitor layer is about 300 mgs to about 400 mgs where the preferred weight is about 300 mgs. The optional film coating can be Opadry® II. In a preferred embodiment, the SGLT2 inhibitor is dapagliflozin or dapagliflozin (S) PGS.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 0.5-4% dapagliflozin or dapagliflozin (S) propylene glycol hydrate; about 14-18% lactose anhydrous; about 72-80% microcrystalline cellulose 302; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 1.7% dapagliflozin (S) PGS, about 16% lactose anhydrous, about 56-64% microcrystalline cellulose 302, about 13-19% pregelatinized starch, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 1.7% dapagliflozin (S) PGS, about 16% lactose anhydrous, about 66% microcrystalline cellulose 302, about 10% hydroxypropyl cellulose, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 72-82% metformin hydrochloride (HCl); about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate. The SGLT2 inhibitor formulation comprises about 1.7% dapagliflozin (S) PGS, about 16% lactose anhydrous, about 61% microcrystalline cellulose 302, about 15% mannitol, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 76.6% metformin hydrochloride (HCl); about 3.84% sodium carboxymethyl cellulose; about 18% hydroxypropyl methylcellulose 2208; about 0.75-

1.25% silicon dioxide or about 0.25-0.75% colloidal silicon dioxide; and about 0.53% magnesium stearate. The SGLT2 inhibitor formulation comprises about 0.8% dapagliflozin or dapagliflozin (S) propylene glycol hydrate; about 16% lactose anhydrous; about 77% microcrystalline cellulose 302; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 76.6% metformin hydrochloride (HCl); about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate. The SGLT2 inhibitor formulation comprises about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 76.6% metformin hydrochloride (HCl); about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate. The SGLT2 inhibitor formulation comprises about 3.4% dapagliflozin or dapagliflozin (S) propylene glycol hydrate, about 16% lactose anhydrous; about 74% microcrystalline cellulose 302; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 76.6% metformin hydrochloride (HCl); about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate. The SGLT2 inhibitor formulation comprises about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 76.6% metformin hydrochloride (HCl); about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate. The SGLT2 inhibitor formulation comprises about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 76.6% metformin hydrochloride (HCl); about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate. The SGLT2 inhibitor formulation comprises about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the reduced mass metformin XR (1000 mgs) formulation comprises about 76.6% metformin hydrochloride (HCl); about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate. The SGLT2 inhibitor formulation comprises about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate. The total weight of the SGLT2 inhibitor layer is about 300 mgs to about 400 mgs where the preferred weight is about 300 mgs. The film coating can be Opadry® II.

The present invention also provides bilayer tablets comprising metformin XR (500 mgs) formulations, SGLT2 inhibitor (2.5, 5.0, 10.0 mgs) formulations, and optionally a film coating. The metformin XR 500 mg formulations comprise metformin HCl, sodium carboxymethyl cellulose, hydroxypropyl methylcellulose, microcrystalline cellulose, magnesium stearate, and optionally silicon dioxide or colloidal silicon dioxide. The SGLT2 inhibitor formulation comprises the SGLT2 inhibitor, lactose anhydrous, microcrystalline cellulose, crospovidone, silicon dioxide, and magnesium stearate. For the second layer, pregelatinized starch, hydroxypropyl cellulose, or mannitol can be used to substitute a portion of the microcrystalline cellulose. The total weight of the SGLT2 inhibitor layer is about 300 mgs to about 400 mgs where the preferred weight is about 300 mgs. The optional film coating can be Opadry® II. In a preferred embodiment, the SGLT2 inhibitor is dapagliflozin, dapagliflozin (S) PGS, or dapagliflozin (R) PGS.

In another aspect, the present invention provides a bilayer tablet wherein the metformin XR (500 mgs) formulation comprises about 40-60% metformin hydrochloride (HCl), about 4-6% sodium carboxymethyl cellulose, about 30-40% hydroxypropyl methylcellulose 2208, about 0.1-1.5% hydroxypropyl methylcellulose 2910, about 5-15% microcrystalline cellulose, about 0.75-1.25% silicon dioxide or about 0.25%-0.75% colloidal silicon dioxide, and about 0.05-5% magnesium stearate. The SGLT2 inhibitor formulation comprises about 0.1-10% SGLT2 inhibitor, about 5-30% lactose anhydrous, about 40-90% microcrystalline cellulose 302, about 0-25% pregelatinized starch, about 0-20% hydroxypropyl cellulose EXF, about 0-25% mannitol (pearlitol SD 200), about 1-10% crospovidone, about 0.1-5% silicon dioxide, and about 0.1-5% magnesium stearate. The total weight of the SGLT2 inhibitor layer is about 300 mgs to about 400 mgs where the preferred weight is about 300 mgs. The optional film coating can be Opadry® II. In a preferred embodiment, the SGLT2 inhibitor is dapagliflozin or dapagliflozin (S) PGS.

In another aspect, the present invention provides a bilayer tablet wherein the metformin XR (500 mgs) formulation comprises about 45-50% metformin hydrochloride (HCl), about 4-6% sodium carboxymethyl cellulose, about 30-40% hydroxypropyl methylcellulose 2208, about 0.1-1.5% hydroxypropyl methylcellulose 2910, about 5-15% microcrystalline cellulose, about 0.75-1.25% silicon dioxide or about 0.25%-0.75% colloidal silicon dioxide, and about 0.05-5% magnesium stearate. The SGLT2 inhibitor formulation comprises about 0.1-10% SGLT2 inhibitor, about 5-30% lactose anhydrous, about 40-90% microcrystalline cellulose 302, about 0-25% pregelatinized starch, about 0-20% hydroxypropyl cellulose EXF, about 0-25% mannitol (pearlitol SD 200), about 1-10% crospovidone, about 0.1-5% silicon dioxide, and about 0.1-5% magnesium stearate. The total weight of the SGLT2 inhibitor layer is about 300 mgs to about 400 mgs where the preferred weight is about 300 mgs. The optional film coating can be Opadry® II. In a preferred embodiment, the SGLT2 inhibitor is dapagliflozin or dapagliflozin (S) PGS.

In another aspect, the present invention provides a bilayer tablet wherein the metformin XR (500 mgs) formulation comprises about 45-50% metformin hydrochloride (HCl), about 4-6% sodium carboxymethyl cellulose, about 30-40% hydroxypropyl methylcellulose 2208, about 0.1-1.5% hydroxypropyl methylcellulose 2910, about 5-15% microcrystalline cellulose, about 0.75-1.25% silicon dioxide or about 0.25%-0.75% colloidal silicon dioxide, and about 0.05-5% magnesium stearate. The SGLT2 inhibitor formulation comprises about 0.5-4% dapagliflozin or dapagliflozin (S) propylene glycol hydrate; about 14-18% lactose anhydrous; about 72-80% microcrystalline cellulose 302; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (500 mgs) formulation comprises about 45-50% metformin hydrochloride (HCl), about 4-6% sodium carboxymethyl cellulose, about 30-40% hydroxypropyl methylcellulose 2208, about 0.1-1.5% hydroxypropyl methylcellulose 2910, about 5-15% microcrystalline cellulose, about 0.75-1.25% silicon dioxide or about 0.25%-0.75% colloidal silicon dioxide, and about 0.05-5% magnesium stearate. The SGLT2 inhibitor formulation comprises about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (500 mgs) formulation comprises about 45-50% metformin hydrochloride (HCl), about 4-6% sodium carboxymethyl cellulose, about 30-40% hydroxypropyl methylcellulose 2208, about 0.1-1.5% hydroxypropyl methylcellulose 2910, about 5-15% microcrystalline cellulose, about 0.75-1.25% silicon dioxide or about 0.25%-0.75% colloidal silicon dioxide, and about 0.05-5% magnesium stearate. The SGLT2 inhibitor formulation comprises about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (500 mgs) formulation comprises about 45-50% metformin hydrochloride (HCl), about 4-6% sodium carboxymethyl cellulose, about 30-40% hydroxypropyl methylcellulose 2208, about 0.1-1.5% hydroxypropyl methylcellulose 2910, about 5-15% microcrystalline cellulose, about 0.75-1.25% silicon dioxide or about 0.25%-0.75% colloidal silicon dioxide, and about 0.05-5% magnesium stearate. The SGLT2 inhibitor formulation comprises about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate. The total weight of the SGLT2 inhibitor layer is about 300 mgs to about 400 mgs where the preferred weight is about 300 mgs. The film coating can be Opadry® II.

In another aspect, the present invention provides a bilayer tablet wherein the metformin XR (500 mgs) formulation comprises about 45-50% metformin hydrochloride (HCl), about 4-6% sodium carboxymethyl cellulose, about 30-40% hydroxypropyl methylcellulose 2208, about 0.1-1.5% hydroxypropyl methylcellulose 2910, about 5-15% microcrystalline cellulose, about 0.75-1.25% silicon dioxide or about 0.25%-0.75% colloidal silicon dioxide, and about 0.05-5% magnesium stearate. The SGLT2 inhibitor formulation comprises about 0.5-4% dapagliflozin (S) PGS, about 16% lactose anhydrous, about 74-77% microcrystalline cellulose 302, about 4% crospovidone, about 1.5% silicon dioxide, and about 1% magnesium stearate. The total weight of the SGLT2 inhibitor layer is about 300 mgs to about 400 mgs where the preferred weight is about 300 mgs. The film coating can be Opadry® II.

The SGLT2 percentages listed above correspond to the active ingredient. The preferred active ingredient is dapagliflozin or dapagliflozin (S) propylene glycol hydrate. It is to be understood that the above percentages (amount) will be higher for dapagliflozin as the propylene glycol hydrate than as the non-solvate/hydrate.

Different forms of the antidiabetic agent metformin are suitable for use in the formulations of the present invention's bilayer tablets including pharmaceutically acceptable salts thereof such as the hydrochloride, hydrobromide, fumarate, succinate, p-chlorophenoxy acetate or embonate. The fumarate and succinate salts are preferably metformin (2:1) fumarate, and metformin (2:1) succinate. Metformin hydrochloride is preferred.

The present invention also contemplates coated bilayer tablets wherein the coating comprises saxagliptin or a pharmaceutically acceptable salt thereof Saxagliptin as the free base, as the monohydrate, or as the hydrochloride is preferred. The coated tablet comprises a tablet core, a first coating, a second coating, and optionally a third coating. The tablet core comprises metformin, preferably metformin hydrochloride. The first and second coating optionally comprises saxagliptin wherein at least one of the first and second coatings comprises saxagliptin. The third coating is an optional outer protective coating. Saxagliptin, shown below, can be prepared as described in U.S. Pat. No. 6,395,767, herein incorporated by reference in its entirety for any purpose. The first and second coatings are prepared in a similar manner to the preparation of the inner seal coating layer or the middle (drug) coating layer described in WO 2005/117841, herein incorporated by reference in its entirety for any purpose. The third coating is prepared in a similar manner to the preparation of the outer protective coating layer described in WO 2005/117841.

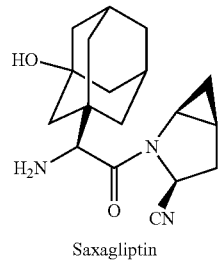 [SMILES: N#C[C@@H]1C[C@@H]2C[C@@H]2N1C(=O)[C@@H](N)C12CC3CC(CC(O)(C3)C1)C2]

Saxagliptin

The first coating includes up to 95% of polymer based on the weight of the first coating layer. The formulation will contain at least one coating layer polymer and a coating solvent, preferably the solvent is water used for processing and removed by drying. The first coating layer polymer may be hydroxypropyl methylcellulose, polyvinyl alcohol (PVA), ethyl cellulose, methacrylic polymers or hydroxypropyl cellulose, preferably PVA. The first coating optionally includes saxagliptin within the range from about 0.5 to about 70%, preferably from about 30 to about 50% by weight based on the weight of the second coating layer. The first coating may include: optionally a plasticizer such as triacetin, diethyl phthalate, tributyl sebacate or polyethylene glycol (PEG), preferably PEG; an anti-adherent or glidant such as talc, fumed silica or magnesium stearate; and an opacifying agent such as titanium dioxide. The coating layer may also include iron oxide based colorants. The coating material is commercially available under the trade name Opadry® HP or Opadry® II white.

The second coating is similar in composition to the first coating and preferably includes saxagliptin.

The third coating is similar in composition to the first coating, only without saxagliptin.

Accordingly, in one aspect, the present invention provides a coated bilayer tablet that comprises: (1) a bilayer tablet core comprising two layers wherein the first layer comprises metformin; and the second layer comprises an SGLT2 inhibitor; wherein the second layer is about 300 to about 400 mgs; (2) a first coating that coats the bilayer tablet core and optionally comprises saxagliptin; (3) a second coating that coats the first coating and optionally comprises saxagliptin; and (4) optionally a third coating that coats the second coating; wherein at least one of the first coating and the second coating comprises saxagliptin.

In one aspect, the present invention provides a coated bilayer tablet that comprises: (1) a bilayer tablet core wherein the first layer comprises about 64-82% metformin hydrochloride, about 3-5% sodium carboxymethyl cellulose; about 15-30% hydroxypropyl methylcellulose; about 0.1-0.75% magnesium stearate; and about 0-2% silicon dioxide or 0-1.5% colloidal silicon dioxide; and the second layer comprises about 0.5-4% dapagliflozin or dapagliflozin (S) propylene glycol hydrate; about 14-18% lactose anhydrous; about 50-80% microcrystalline cellulose; about 0-20% pregelatinized starch; about 0-20% mannitol; about 0-15% hydroxypropyl cellulose; about 2-6% crospovidone; about 0.5-2.5% silicon dioxide; and about 0.5-2% magnesium stearate; wherein the second layer is about 300 to about 400 mgs; (2) the first coating comprises a polyvinyl alcohol based polymer; (3) the second coating comprises saxagliptin and a polyvinyl alcohol based polymer; and (4) the third coating comprises a polyvinyl alcohol based polymer.

In one aspect, the present invention provides a coated bilayer tablet that comprises: (1) a bilayer tablet core wherein the first layer comprises about 67-71% metformin hydrochloride, about 3-5% sodium carboxymethyl cellulose, about 25-29% hydroxypropyl methylcellulose 2208, and about 0.1-0.75% magnesium stearate; and the second layer comprises:
(A) about 0.5-4% dapagliflozin or dapagliflozin (S) propylene glycol hydrate: about 14-18% lactose anhydrous; about 72-80% microcrystalline cellulose 302; about 2-6% crospovidone; about 0.5-2.5% silicon dioxide; and about 0.5-1.5% magnesium stearate;
(B) about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6% crospovidone; about 0.5-2.5% silicon dioxide; and about 0.5-1.5% magnesium stearate;
(C) about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate; or
(D) about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate; wherein the second layer is about 300 to about 400 mgs; (2) the first coating comprises Opadry® HP; (3) the second coating comprises saxagliptin and Opadry® HP; and (4) the third coating comprises Opadry® HP.

In one aspect, the present invention provides a coated bilayer tablet that comprises: (1) a bilayer tablet core wherein the first layer comprises about 69% metformin hydrochloride, about 3.5% sodium carboxymethyl cellulose, about 27% hydroxypropyl methylcellulose 2208, and about 0.48% magnesium stearate and the second layer comprises:
(A) about 0.8% dapagliflozin or dapagliflozin (S) propylene glycol hydrate; about 16% lactose anhydrous; about 77% microcrystalline cellulose 302; about 4% crospovidone; about 1.5% silicon dioxide; and about 1% magnesium stearate;
(B) about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate;
(C) about 3.4% dapagliflozin or dapagliflozin (S) propylene glycol hydrate; about 16% lactose anhydrous; about 74% microcrystalline cellulose 302; about 4% crospovidone; about 1.5% silicon dioxide; and about 1% magnesium stearate;
(D) about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate;

(E) about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate;

(F) about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate; or (G) about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate; wherein the second layer is about 300 to about 400 mgs;

(2) the first coating comprises Opadry® HP; (3) the second coating comprises saxagliptin and Opadry® HP; and (4) the third coating comprises Opadry® HP.

In one aspect, the present invention provides a coated bilayer tablet that comprises: (1) a bilayer tablet core wherein the first layer comprises about 72-82% metformin hydrochloride; about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate; the second layer comprises:

(A) about 0.5-4% dapagliflozin or dapagliflozin (S) propylene glycol hydrate; about 14-18% lactose anhydrous; about 72-80% microcrystalline cellulose 302; about 2-6% crospovidone; about 0.5-2.5% silicon dioxide; and about 0.5-1.5% magnesium stearate;

(B) about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6.00% crospovidone; about 0.5-2.5% silicon dioxide; and about 0.5-1.5% magnesium stearate;

(C) about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate; or (D) about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate; wherein the second layer is about 300 to about 400 mgs;

(2) the first coating comprises Opadry® HP; (3) the second coating comprises saxagliptin and Opadry® HP; and (4) the third coating comprises Opadry® HP.

In one aspect, the present invention provides a coated bilayer tablet that comprises: (1) a bilayer tablet core wherein the first layer comprises about 76.6% metformin hydrochloride; about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate; the second layer comprises:

(A) about 0.8% dapagliflozin or dapagliflozin (S) propylene glycol hydrate; about 16% lactose anhydrous; about 77% microcrystalline cellulose 302; about 4% crospovidone; about 1.5% silicon dioxide; and about 1% magnesium stearate;

(B) about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate;

(C) about 3.4% dapagliflozin or dapagliflozin (S) propylene glycol hydrate; about 16% lactose anhydrous; about 74% microcrystalline cellulose 302; about 4% crospovidone; about 1.5% silicon dioxide; and about 1% magnesium stearate;

(D) about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate;

(E) about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate;

(F) about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate; or (G) about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate; wherein the second layer is about 300 to about 400 mgs;

(2) the first coating comprises Opadry® HP; (3) the second coating comprises saxagliptin and Opadry® HP; and (4) the third coating comprises Opadry® HP.

In one aspect, the present invention provides a coated tablet that comprises a tablet core coated with a first coating optionally containing saxagliptin, a second coating optionally containing saxagliptin, and an optional third coating. The tablet core comprises metformin where metformin hydrochloride is preferred. At least one of the first and second coatings contains saxagliptin. The first and second coatings are prepared in a similar manner to the preparation of the inner seal coating layer or the middle (drug) coating layer described in WO 2005/117841. The third coating is prepared in a similar manner to the preparation of the outer protective coating layer described in WO 2005/117841.

In another aspect, the present invention provides a coated tablet comprising: (1) a tablet core that comprises metformin; (2) a first coating that coats the tablet core and optionally comprises saxagliptin; (3) a second coating that coats the first coating and optionally comprises saxagliptin; and (4) optionally a third coating that coats the second coating; where at least one of the first coating and the second coating comprises saxagliptin.

In another aspect, the present invention provides a coated tablet comprising: (1) a tablet core that comprises about 72-82% metformin hydrochloride; about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate; (2) a first coating that comprises a polyvinyl alcohol based polymer; (3) a second coating that comprises saxagliptin and a polyvinyl alcohol based polymer; and (4) a third coating that comprises a polyvinyl alcohol based polymer.

In another aspect, the present invention provides a coated tablet comprising: (1) a tablet core that comprises about 76.6% metformin hydrochloride; about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate; (2) a first coating that comprises Opadry® HP; (3) a second coating that comprises saxagliptin and Opadry® HP; and (4) a third coating that comprises Opadry® HP.

In another aspect, the present invention provides a coated tablet comprising: (1) a tablet core that comprises about 76.6% metformin hydrochloride; about 3.84% sodium carboxymethyl cellulose; about 18% hydroxypropyl methylcellulose 2208; about 1% silicon dioxide; and about 0.53% magnesium stearate; (2) a first coating that comprises Opadry® HP; (3) a second coating that comprises saxagliptin and Opadry® HP; and (4) a third coating that comprises Opadry® HP.

In another aspect, the present invention provides a coated tablet comprising: (1) a tablet core that comprises about 76.6% metformin hydrochloride; about 3.84% sodium carboxymethyl cellulose; about 18% hydroxypropyl methylcellulose 2208; about 1% silicon dioxide; and about 0.53% magnesium stearate; (2) a first coating that comprises about 2% Opadry® HP; (3) a second coating that comprises about 1.25% saxagliptin and about 10% Opadry® HP; and (4) a third coating that comprises about 2% Opadry® HP.

In another aspect, the present invention provides combination therapies that comprise the bilayer tablet of the present invention in combination with one or more: anti-diabetics; anti-hyperglycemic agents; hypolipidemic/lipid lowering agents; anti-obesity agents; anti-hypertensive agents appetite suppressants; insulin secretagogues, insulin sensitizers, glucokinase activators, glucocorticoid antagonist, fructose 1,6-bis phosphatase inhibitors, AMP kinase activators, modulators of the incretin pathway such as incretin secretagogues such as GPR119 or GPR40 agonists, incretin mimics such as Byetta, and incretin potentiators, bile acid sequestrants or bile acid receptor agonists such as TGR5 agonists, dopamine receptor agonists such as Cycloset, aldose reductase inhibitors PPARγ agonists, PPARα agonists, PPARγ antagonists or agonists, PPARα/γ dual agonists, 11-β-HSD-1 inhibitors, dipeptidyl peptidase IV (DPP4) inhibitors other than saxagliptin, SGLT2 inhibitors other than dapagliflozin, glucagon-like peptide-1 (GLP-1), GLP-1 agonists, and PTP-1B inhibitors. Also weight loss agents acting to decreasing food intake such as sibutrimine, CB1 antagonists, 5HT2C agonists, MCHR1 antagonists, and agents which decrease nutrient absorption (such as lipase inhibitors (Orlistat)), and agents which increase energy expenditure such as thyromimetics, or slow GI motility such as amylin mimetics or ghrelin antagonists.

Examples of suitable anti-diabetic agents for use in combination with the formulations of the present invention include, but are not limited to, alpha glucosidase inhibitors (acarbose or miglitol), insulins (including insulin secretagogues or insulin sensitizers), meglitinides (repaglinide), sulfonylureas (glimepiride, glyburide, gliclazide, chlorpropamide and glipizide), biguanide/glyburide combinations (Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), GPR-119 modulators, GPR 40 modulators, glucokinase inhibitors, glucagon-like peptide-1 (GLP-1) and other agonists of the GLP-1 receptor, SGLT2 inhibitors other than dapagliflozin, and dipeptidyl peptidase IV (DPP4) inhibitors other than saxagliptin.

Other suitable thiazolidinediones include, but are not limited to, MCC-555 (disclosed in U.S. Pat. No. 5,594,016, Mitsubishi), faraglitazar (GI-262570, Glaxo-Wellcome), englitazone (CP-68722, Pfizer) or darglitazone (CP-86325, Pfizer; isaglitazone, MIT/Johnson& Johnson), reglitazar OTT-501, (JPNT/Pharmacia & Upjohn), rivoglitazone (R-119702, Sankyo/WL), liraglutide (NN-2344, Dr. Reddy/NN), and (Z)-1,4-bis-4-[(3,5-dioxo-1,2,4-oxadiazolidin-2-yl-methyl)]phenoxybut-2-ene (YM-440, Yamanouchi).

Examples of PPAR-alpha agonists, PPAR-gamma agonists and PPAR alpha/gamma dual agonists include, but are not limited to, muraglitazar, peliglitazar, tesaglitazar AR-H039242 (Astra/Zeneca), GW-501516 (Glaxo-Wellcome), KRP297 (Kyorin Merck), as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998); WO 01/21602 and in U.S. Pat. No. 6,414,002 and U.S. Pat. No. 6,653,314, the disclosures of which are incorporated herein by reference in their entireties, employing dosages as set out therein. In one embodiment, the compounds designated as preferred in the cited references are preferred for use herein.

Suitable aP2 inhibitors include, but are not limited to, those disclosed in U.S. application Ser. No. 09/391,053, filed Sep. 7, 1999, and in U.S. Pat. No. 6,548,529, the disclosures of which are incorporated herein by reference in their entireties, employing dosages as set out therein.

Suitable DPP4 inhibitors include, but are not limited to, sitagliptin and vildagliptin, as well as those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996), the compounds disclosed in U.S. application Ser. No. 10/899,641, all of which are incorporated herein by reference in their entireties, employing dosages as set out in the above references.

Suitable SGLT2 inhibitors contemplated by the present invention's bilayer coated tablet and combination therapy with the present invention's bilayer tablet include sergliflozin, remogliflozin, remogliflozin etabonate, canagliflozin, BI-10773 and BI-44847, ASP-1941, R-7201, LX-4211, YM-543, AVE 2268, TS-033 or SGL-0100, and the compounds disclosed in U.S. Pat. No. 7,589,193, WO2007007628, EP2009010, WO200903596, US2009030198, U.S. Pat. No. 7,288,528 and US 2007/0197623, herein incorporated by reference in their entirety for any purpose. The following SGLT2 inhibitors are preferred

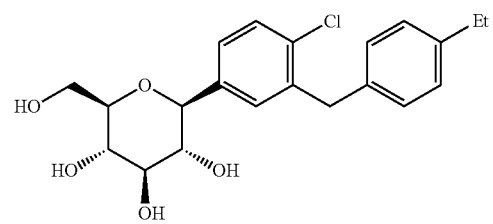
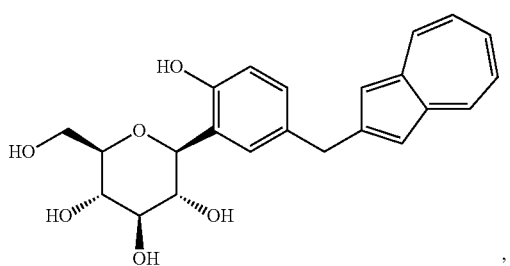
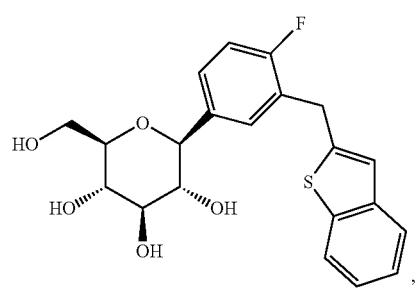
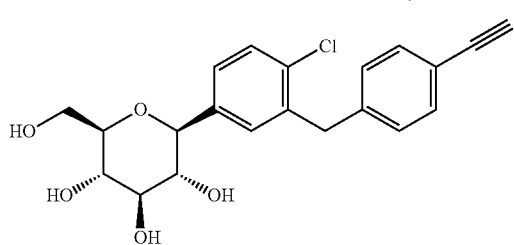
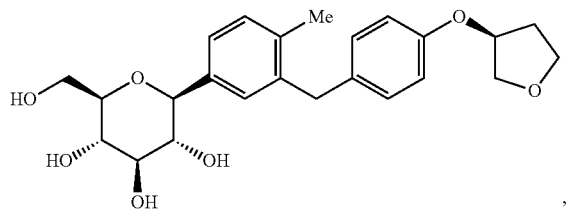
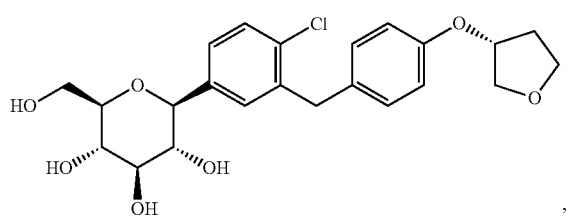
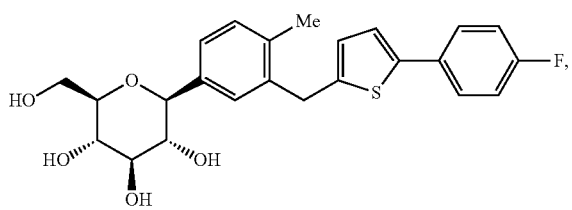
-continued
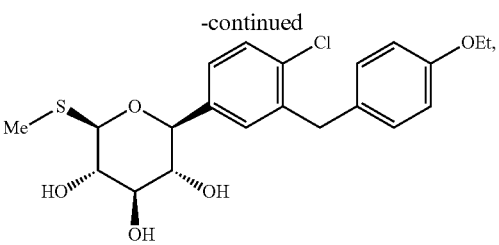
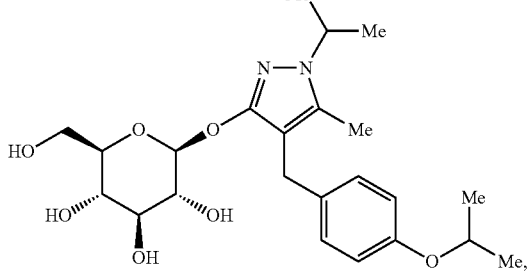
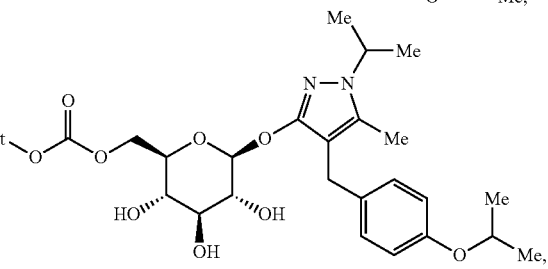
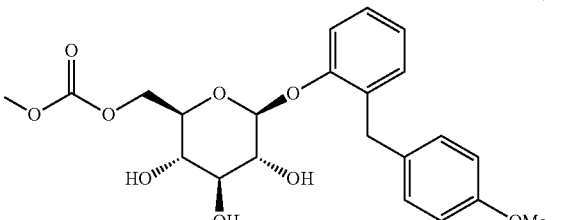
and
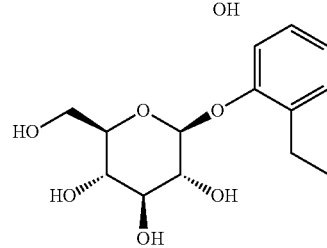
Suitable meglitinides include nateglinide (Novartis) or KAD1229 (PF/Kissei).
Examples of suitable anti-hyperglycemic agents for use in combination with the formulations of the present invention include, but are not limited to, glucagon-like peptide-1 (GLP-1) such as GLP-1(1-36) amide, GLP-1(7-36) amide, GLP-1

(7-37) (as disclosed in U.S. Pat. No. 5,614,492, incorporated herein by reference in its entirety), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671, incorporated herein by reference in its entirety.

Examples of suitable hypolipidemic/lipid lowering agents for use in combination with the formulations of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na Vbile acid co-transporter inhibitors, up-regulators of LDL receptor activity, bile acid sequestrants, cholesterol ester transfer protein (e.g., CETP inhibitors, such as torcetrapib (CP-529414, Pfizer) and JTT-705 (Akros Pharma)), PPAR agonists (as described above) and/or nicotinic acid and derivatives thereof. The hypolipidemic agent can be an up-regulator of LD2 receptor activity, such as 1(3H)-isobenzofuranone,3-(13-hydroxy-10-oxotetradecyl)-5,7-dimethoxy-(MD-700, Taisho Pharmaceutical Co. Ltd) and cholestan-3-o1,4-(2-propenyl)-(3a,4a,5a)-(LY295427, Eli Lilly). Preferred hypolipidemic agents include pravastatin, lovastatin, simvastatin, atorvastatin, fluvastatin, cerivastatin, atavastatin and rosuvastatin (ZD-4522), for example.

Examples of MTP inhibitors that can be employed as described above include, but are not limited to, those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440, all of which are incorporated herein by reference in their entireties.

Examples of HMG CoA reductase inhibitors that can be employed in combination with the formulations of the invention include, but are not limited to, mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other suitable HMG CoA reductase inhibitors that can be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, rosuvastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506, 219 and 5,691,322. All of the cited references are incorporated herein by reference in their entireties. In addition, phosphinic acid compounds useful in inhibiting HMG CoA reductase, such as those disclosed in GB 2205837, are suitable for use in combination with the formulations of the present invention.

Examples of squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp. 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996). Other squalene synthetase inhibitors suitable for use herein include the terpenoid pyrophosphates disclosed by P. Ortiz de Montellano et al, J. Med. Chem., 1977, 20, 243-249; the farnesyl diphosphate analog A and presqualene pyrophosphate (PSQ-PP) analogs as disclosed by Corey and Volante, J. Am. Chem. Soc., 1976, 98, 1291-1293; phosphinylphosphonates reported by McClard, R. W. et al, J.A.C.S., 1987, 109, 5544; and cyclopropanes reported by Capson, T. L., PhD dissertation, June 1987, Dept. Med. Chem. U of Utah, Abstract, Table of Contents, pp 16, 17, 40-43, 48-51, Summary. All of the cited references are incorporated herein by reference in their entireties.

Examples of fibric acid derivatives that can be employed in combination the formulations of the invention include, but are not limited to, fenofibrate, gemfibrozil, clofibrate, bezafibrate, ciprofibrate, clinofibrate and the like, probucol, and related compounds, as disclosed in U.S. Pat. No. 3,674,836, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents. In one embodiment, the fibric acid derivative is probucol or gemfibrozil. All of the cited references are incorporated herein by reference in their entireties.

Examples of ACAT inhibitors that can be employed in combination with the formulations of the invention include, but are not limited to, those disclosed in Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. The first water-soluble ACAT inhibitor with lipid-regulating activity. Inhibitors of acyl-CoA:cholesterol acyltransferase (ACAT). Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd). All of the cited references are incorporated herein by reference in their entireties.

Examples of suitable cholesterol absorption inhibitors for use in combination with the formulations of the invention include, but are not limited to, SCH48461 (Schering-Plough), as well as those disclosed in Atherosclerosis 115, 45-63 (1995) and J. Med. Chem. 41, 973 (1998), incorporated herein by reference in its entirety.

Examples of suitable ileal $Na^+$/bile acid co-transporter inhibitors for use in combination with the formulations of the invention include, but are not limited to, compounds as disclosed in Drugs of the Future, 24, 425-430 (1999), incorporated herein by reference in its entirety.

Examples of lipoxygenase inhibitors that can be employed in combination with the formulations of the invention include, but are not limited to, 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al., "15-Lipoxygenase and its Inhibition: A Novel Therapeutic Target for Vascular Disease", Current Pharmaceutical Design, 1999, 5, 11-20. All of the cited references are incorporated herein by reference in their entireties.

Examples of suitable anti-hypertensive agents for use in combination with the formulations of the present invention include, but are not limited to, beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates. All of the cited references are incorporated herein by reference in their entireties.

Examples of suitable anti-obesity agents for use in combination with the formulations of the present invention include, but are not limited to, beta 3 adrenergic agonists, lipase inhibitors, serotonin (and dopamine) reuptake inhibitors, thyroid receptor beta drugs, 5HT2C agonists, (such as Arena APD-356); MCHR1 antagonists, such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, ciliary neurotrophic factors (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and anorectic agents.

Beta 3 adrenergic agonists that can be optionally employed in combination with formulations of the present invention include, but are not limited to, AJ9677 (Takeda/Dainippon), L750355 (Merck), CP331648 (Pfizer,) or other known beta 3 agonists, as disclosed in U.S. Pat. Nos. 5,541,204, 5,770,615, 5,491,134, 5,776,983 and 5,488,064, all of which are incorporated herein by reference in their entireties.

Examples of lipase inhibitors that can be employed in combination with formulations of the present invention include, but are not limited to, orlistat and ATL-962 (Alizyme).

Serotonin (and dopamine) reuptake inhibitors (or serotonin receptor agonists) that can be employed in combination with the formulations of the present invention include, but are not limited to, BVT-933 (Biovitrum), sibutramine, topiramate (Johnson & Johnson) and axokine (Regeneron).

Examples of thyroid receptor beta compounds that can be employed in combination with formulations of the present invention include, but are not limited to, thyroid receptor ligands, such as those disclosed in WO 97/21993 (U. Cal SF), WO 99/00353 (KaroBio) and WO 00/039077 (KaroBio), incorporated herein by reference it their entireties.

Examples of monoamine reuptake inhibitors that can be employed in combination with the formulations of the present invention include, but are not limited to, fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol.

Anorectic agents that can be employed in combination with the formulations of the present invention include, but are not limited to, topiramate (Johnson & Johnson), dexamphetamine, phentermine, phenylpropanolamine and mazindol.

The aforementioned patents and patent applications are incorporated herein by reference.

Where any of the formulations of the invention are used in combination with other therapeutic agent(s), the other therapeutic agent(s) can be used, for example, in the amounts indicated in the Physician's Desk Reference, as in the cited patents and patent applications set out above, or as otherwise known and used by one of ordinary skill in the art.

The present invention contemplates a bilayer tablet that comprises (1) a reduced mass metformin formulation; (2) a formulation with canagliflozin; and (3) optionally a coating. Accordingly, in one aspect, the present invention provides a bilayer tablet wherein (1) the first layer comprises about 72-82% metformin hydrochloride; about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate; (2) the second layer comprises canagliflozin; and (3) the optional coating comprises Opadry® II.

In another aspect, the present invention provides a bilayer tablet wherein (1) the first layer comprises about 76.6% metformin hydrochloride; about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate; (2) the second layer comprises canagliflozin; and (3) the optional coating comprises Opadry® II.

In another aspect, the present invention provides a bilayer tablet wherein (1) the first layer comprises about 76.6% metformin hydrochloride; about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate; (2) the second layer comprises canagliflozin; and (3) the optional coating comprises Opadry® II.

Examples of bulking agents or fillers suitable for use herein include, but are not limited to, cellulose derivatives, such as microcrystalline cellulose or wood cellulose (including microcrystalline cellulose 302), lactose, lactose anhydrous, sucrose, starch, pregelatinized starch, dextrose, mannitol (including mannitol Pearlitol SD 200), fructose, xylitol, sorbitol, corn starch, modified corn starch, inorganic salts such as calcium carbonate, calcium phosphate, dicalcium phosphate, calcium sulfate, dextrin/dextrates, maltodextrin, compressible sugars, and other known bulking agents or fillers, and/or mixtures of two or more thereof. Several types of microcrystalline cellulose are suitable for use in the formulations described herein, for example, microcrystalline cellulose selected from the group consisting of Avicel® types: PH101, PH102, PH103, PH105, PH 112, PH113, PH200, PH301, and other types of microcrystalline cellulose, such as silicified microcrystalline cellulose. Several types of lactose are suitable for use in the formulations described herein, for example, lactose selected from the group consisting of anhydrous lactose, lactose monohydrate, lactose fast flo, directly compressible anhydrous lactose, and modified lactose monohydrate.

Examples of binders suitable for use herein include, but are not limited to, carboxymethyl cellulose (including sodium carboxymethyl cellulose), hydroxypropyl cellulose (including hydroxypropyl cellulose EXF), corn starch, pregelatinized starch, modified corn starch, polyvinyl pyrrolidone (PVP), hydroxypropyl methylcellulose (HPMC) (including hydroxypropyl methylcellulose 2208), lactose, gum acacia, ethyl cellulose, cellulose acetate, as well as a wax binder such as carnauba wax, paraffin, spermaceti, polyethylenes or microcrystalline wax, as well as other conventional binding agents and/or mixtures of two or more thereof.

Examples of disintegrants suitable for use herein include, but are not limited to, croscarmellose sodium, crospovidone, starch, potato starch, pregelatinized starch, corn starch, sodium starch glycolate, microcrystalline cellulose, low substituted hydroxypropyl cellulose and other known disintegrants. Several specific types of disintegrant are suitable for use in the formulations described herein. For example, any grade of crospovidone can be used, including for example crospovidone XL-10, and includes members selected from the group consisting of Kollidon CL®, Polyplasdone XL®, Kollidon CL-M®, Polyplasdone XL-10®, and Polyplasdone INF-10®. In one embodiment, the disintegrant, if present, of the stock granulation is sodium starch glycolate, croscarmellose sodium and/or crospovidone.

Examples of lubricants suitable for use herein include, but are not limited to, magnesium stearate, zinc stearate, calcium stearate, talc, carnauba wax, stearic acid, palmitic acid, sodium stearyl fumarate sodium laurel sulfate, glyceryl palmitostearate, palmitic acid, myristic acid and hydrogenated vegetable oils and fats, as well as other known lubricants, and/or mixtures of two or more thereof.

Examples of glidants and/or anti-adherents suitable for use herein include but are not limited to, silicon dioxide, colloidal silicon dioxide, magnesium silicate, magnesium trisilicate, talc, and other forms of silicon dioxide, such as aggregated silicates and hydrated silica.

Examples of suitable release modifiers include, but are not limited to, hydroxypropyl methylcellulose, polyvinyl alcohol (PVA), ethyl cellulose, methacrylic polymers, hydroxypropyl cellulose, starches, gums, cellulose ethers, protein derived materials, nylon, acrylic resins, polylactic acid, polyvinylchloride, polyvinylpyrrolidones, and cellulose acetate phthalate.

In one aspect, the present invention provides methods of treating diseases or disorders associated with SGLT2 activity comprising administering to a mammal, preferably a human, in need of such treatment a therapeutically effective amount of a bilayer tablet comprising a metformin XR formulation or a reduced mass metformin XR formulation, an SGLT2 inhibitor formulation, and optionally a film coating. The bilayer tablets of the present invention, as described herein, can be administered to mammals, preferably humans, for treating diabetes (including type I and type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension. In a preferred embodiment, the bilayer tablet formulations of the present invention are administered to humans for treating type II diabetes.

In another aspect, the present invention provides a use of a bilayer tablet comprising a metformin XR formulation or a reduced mass metformin XR formulation, an SGLT2 inhibitor formulation, and optionally a film coating for preparing, or for the manufacture of, a medicament for treating diabetes (including type I and type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension.

DEFINITIONS

The term "about" as used herein means a deviation within 10%, more preferably within 5%, and even more preferably, within 2% of the numbers reported.

The term "dapagliflozin" as used herein means the compound of Example 1 and includes pharmaceutically acceptable salts thereof.

The term "dapagliflozin (S) PGS" as used herein means the compound of Example 2 dapagliflozin (S) propylene glycol hydrate (1:1:1).

The term "dapagliflozin (R) PGS" as used herein means the compound of Example 3 dapagliflozin (R) propylene glycol hydrate (1:1:1).

The term "metformin extended release" or "metformin XR" as used herein, refers to an amount of metformin HCl that is present in a dosage form that allows for oral controlled release delivery that functions by releasing the payload of drug (metformin HCl) over an extended period of time following administration, while maintaining the desired plasma levels of drug.

The term "Opadry® II" as used here means a film coating for a tablet, including a bilayer tablet, that comprises polyvinyl alcohol, titanium dioxide, polyethylene glycol (PEG), and talc. Opadry® II white 85F18422 is comprised of polyvinyl alcohol, titanium dioxide, polyethylene glycol, and talc. Opadry® II Yellow 85F92582 is comprised of polyvinyl alcohol, titanium dioxide, polyethylene glycol, talc, and yellow iron dioxide.

The term "Opadry® HP" as used here means a film coating for a tablet that comprises 40% polyvinyl alcohol, 20% polyethylene glycol, 15% talc, and 25% titanium dioxide.

Human Studies

In a 24-week phase 3 clinical study, the combination of metformin and dapagliflozin, an SGLT2 inhibitor, reduced glycosylated hemoglobin levels (HbA1c) and fasting plasma glucose (FPG) levels in type II diabetic patients. Glycosylated hemoglobin and fasting plasma glucose levels were inadequately controlled with metformin alone, as compared to placebo plus metformin. The study also showed that individuals receiving dapagliflozin had statistically greater mean reductions in body weight compared to individuals taking placebo.

The study was designed to assess the efficacy and safety of dapagliflozin as an add-on to metformin over 24 weeks in patients with inadequately controlled type 2 diabetes. The data represent findings from a randomized, double-blind, placebo-controlled study of 546 individuals with type 2 diabetes whose HbA1c was greater than or equal to 7.0 percent and less than or equal to 10 percent at baseline. After a two-week lead-in phase, individuals were randomized to one of four separate treatment arms: dapagliflozin 2.5 mg (n=137), dapagliflozin 5 mg (n=137), dapagliflozin 10 mg (n=135), or placebo (n=137). Patients in all arms also received metformin (greater than or equal to 1500 mg/d). The primary endpoint of the study compared mean HbA1c change from baseline for each dapagliflozin treatment arm compared to placebo after 24 weeks. Secondary endpoints included change from baseline in FPG and body weight at week 24 as compared to placebo, and adjusted percentage of individuals treated with dapagliflozin who achieved HbA1c of less than 7 percent at 24 weeks. Exploratory endpoints included body weight decrease of greater than or equal to 5 percent or greater than or equal to 10 percent as well as body weight percent change from baseline.

After 24 weeks, individuals receiving dapagliflozin 2.5 mg, 5 mg and 10 mg plus metformin demonstrated a statistically significant adjusted mean change in HbA1c from baseline of −0.67 percent, −0.70 percent and −0.84 percent, respectively, compared to −0.30 percent for placebo. Individuals treated with dapagliflozin demonstrated a statistically significant adjusted mean change in FPG, a secondary endpoint, from baseline at Week 24: −17.8 mg/dL for dapagliflozin 2.5 mg −21.5 mg/dL for dapagliflozin 5 mg and −23.5 mg/dL/dl for dapagliflozin 10 mg, compared to −6.0 mg/dL for placebo.

The study also evaluated the potential impact of dapagliflozin on weight loss. These findings included data measuring changes in total body weight over the 24-week study period. At 24 weeks, the change in total body weight in kg, a secondary endpoint, was −2.21 kg for dapagliflozin 2.5 mg, −3.04 kg for dapagliflozin 5 mg and −2.86 kg for dapagliflozin 10 mg, compared to −0.89 kg for placebo. Overall, more patients taking dapagliflozin achieved weight losses greater than or equal to 5 percent compared to placebo, an exploratory endpoint.

These results indicate that the combination of an SGLT2 inhibitor, in particular dapagliflozin or dapagliflozin (S) pro-pylene glycol hydrate, with metformin effectively treats hyperglycemia in type II diabetic patients without inducing weight gain.

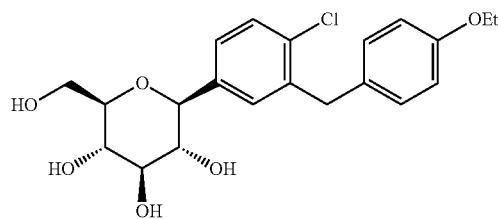 [SMILES: CCOc1ccc(Cc2cc([C@@H]3O[C@H](CO)[C@@H](O)[C@H](O)[C@H]3O)ccc2Cl)cc1]

Example 1

Dapagliflozin-(2S,3R,4R,5S,6R)-2-(4-chloro-3-(4-ethoxybenzyl)phenyl)-6-(hydroxymethyl)tetrahydro-2H-pyran-3,4,5-triol Dapagliflozin can be prepared using similar procedures as described in U.S. Pat. No. 6,515,117 or international published applications no. WO 03/099836 and WO 2008/116179, the disclosures of which are herein incorporated by reference in their entirety for any purpose. SGLT2 $EC_{50}$=1.1 nM.

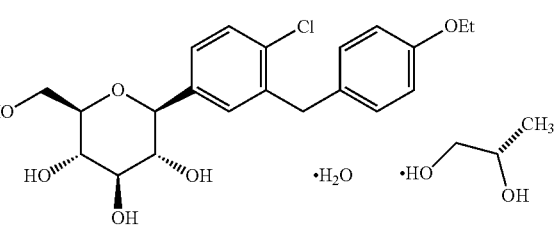

Example 2

Dapagliflozin (S) PGS-(2S,3R,4R,5S,6R)-2-(4-chloro-3-(4-ethoxybenzyl)phenyl)-6-(hydroxymethyl)tetrahydro-2H-pyran-3,4,5-triol (S)-propane-1,2-diol hydrate (1:1:1)

Dapagliflozin (S) propylene glycol hydrate (1:1:1) can be prepared using similar procedures as described in published applications WO 08/002824 and WO 2008/116179, the disclosures of which are herein incorporated by reference in their entirety for any purpose. SGLT2 $EC_{50}$=1.1 nM.

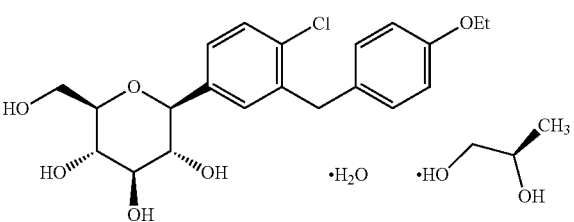

Example 3

Dapagliflozin (R) PGS-(2S,3R,4R,5S,6R)-2-(4-chloro-3-(4-ethoxybenzyl)phenyl)-6-(hydroxymethyl)tetrahydro-2H-pyran-3,4,5-triol

(R)-propane-1,2-diol hydrate (1:1:1)

Dapagliflozin (R) propylene glycol hydrate (1:1:1) can be prepared using similar procedures as described in WO 08/002824 and WO 2008/116179, the disclosures of which are herein incorporated by reference in their entirety for any purpose. SGLT2 $EC_{50}$=1.1 nM.

Example 4

Bilayer tablets containing metformin (1000 mgs) extended release formulation and dapagliflozin (S) PGS (5.00 mgs) immediate release formulation were prepared as described below.

|  | % w/w | amount (mg) |
|---|---|---|
| First Layer |  |  |
| Metformin HCl | 68.97 | 1000 |
| Sodium Carboxymethyl Cellulose | 3.45 | 50.01 |
| Purified water or water for injection | — | q.s.$^{(a)}$ |
| Hydroxypropyl Methylcellulose 2208 | 27.10 | 393 |
| Magnesium Stearate | 0.48 | 7.00 |
| Total Metformin XR | 100 | 1450 |
| Second Layer |  |  |
| Dapagliflozin | 1.67 | 5.00 |
| Lactose Anhydrous | 16.00 | 48.00 |
| Microcrystalline Cellulose 302 | 75.83 | 227.5 |
| Crospovidone | 4.00 | 12.00 |
| Silicon Dioxide | 1.50 | 4.50 |
| Magnesium Stearate | 1.00 | 3.00 |
| Total Dapagliflozin IR | 100 | 300 |
| Total Core Bilayer |  | 1750 |
| Film Coat |  |  |
| Opadry ® II (2.5% weight gain) |  | 43.75 |
| Total Film Coated Tablet |  | 1793.75 |

Metformin Granulation (1000 mgs)

Metformin HCl, 0.5% magnesium stearate, and sodium carboxymethyl cellulose were combined and mixed into a high shear granulator for one minute. Purified water, using a nozzle, was added with stirring for one minute. The wet granulated material was passed through a mill and then dried until the moisture content was 1.0% or less. The dried material containing metformin HCl, 0.5% magnesium stearate, and sodium carboxymethyl cellulose was passed through a mill and discharge into polyethylene-lined drums to provide milled metformin 1 g bulk granulation.

Hydroxypropyl methylcellulose 2208 USP (100,000 centipoise) (methocel K100M Premium) was added to a bin blender and mixed for 60 revolutions. The material was passed through a mill and discharge to provide milled hydroxypropyl methylcellulose 2208 USP.

Metformin (milled 1 g bulk granulation), hydroxypropyl methylcellulose 2208 USP (milled), hydroxypropyl methylcellulose 2208 USP (unmilled), and magnesium stearate were added to a bin blender and mixed for 60 revolutions. The mixed material was discharge into polyethylene-lined drums to provide metformin extended release 1 g bulk granulation.

Dapagliflozin Granulation (2.5, 5.0, 10.0 mgs)

Dapagliflozin (S) PGS was blended with microcrystalline cellulose, anhydrous lactose, a portion of crospovidone, and a portion of silicon dioxide in a suitable tumble mixer and passed through a suitable conical mill. A portion of magnesium stearate (screened) was blended into the mixture and then compacted using an appropriate roller compactor. The compacted mixture was reduced to form granules. The granules were blended with the remaining amount of crospovidone and silicon dioxide in a suitable tumble mixer. The granules were then blended with the remaining amount of magnesium stearate in a suitable tumble mixer.

Bilayer Compression

A bilayer tablet press was with either the metformin XR formulation or the reduced mass metformin XR formulation in the first hopper and the SGLT2 inhibitor formulation that is dapagliflozin (S) PGS granulation (2.5 mg, 5 mg or 10 mg strength) in the second hopper. The tablet press was set to obtain the target weight for the first layer (metformin XR or reduced mass metformin XR). The second hopper was opened and the tablet press was adjusted to obtain the target tablet weight of dapagliflozin and metformin XR or dapagliflozin and reduced mass metformin XR bilayer tablets. Once the target weight was obtained the press was adjusted to obtain the target hardness. Once the hardness was obtained, the manufactured tablets were periodically monitored regarding the weight of the first layer, and the weight, hardness, gauge and friability of the whole tablet. The collect bilayer tablets were film coated with Opadry® II PVA (polyvinyl alcohol).

Example 5

Bilayer tablets containing metformin (1000 mgs) extended release formulation and dapagliflozin (S) PGS (2.5 mgs) immediate release formulation were prepared in a similar manner as described in Example 4.

|  | % w/w | amount (mg) |
|---|---|---|
| First Layer |  |  |
| Metformin HCl | 68.97 | 1000 |
| Sodium Carboxymethyl Cellulose | 3.45 | 5001 |
| Purified water or water for injection | — | q.s.$^{(a)}$ |
| Hydroxypropyl Methylcellulose 2208 | 27.10 | 393 |
| Magnesium Stearate | 0.48 | 7 |
| Total Metformin XR | 100 | 1450 |
| Second Layer |  |  |
| Dapagliflozin | 0.83 | 2.50 |
| Lactose Anhydrous | 16.00 | 48.00 |
| Microcrystalline Cellulose 302 | 76.67 | 230.00 |
| Crospovidone | 4.00 | 12.00 |
| Silicon Dioxide | 1.50 | 4.50 |
| Magnesium Stearate | 1.00 | 3.00 |
| Total Dapagliflozin IR | 100 | 300 |
| Total Core Bilayer |  | 1750 |

Example 6

Bilayer tablets containing metformin (1000 mgs) extended release formulation and dapagliflozin (S) PGS (10.00 mgs)

immediate release formulation were prepared in a similar manner as described in Example 4.

|  | % w/w | amount (mg) |
|---|---|---|
| First Layer | | |
| Metformin HCl | 68.97 | 1000 |
| Sodium Carboxymethyl Cellulose | 3.45 | 50.01 |
| Purified water or water for injection | — | q.s.[a] |
| Hydroxypropyl Methylcellulose 2208 | 27.10 | 393 |
| Magnesium Stearate | 0.48 | 7 |
| Total Metformin XR | 100 | 1450 |
| Second Layer | | |
| Dapagliflozin | 3.33 | 10.00 |
| Lactose Anhydrous | 16.00 | 48.00 |
| Microcrystalline Cellulose 302 | 74.17 | 222.50 |
| Crospovidone | 4.00 | 12.00 |
| Silicon Dioxide | 1.50 | 4.50 |
| Magnesium Stearate | 1.00 | 3.00 |
| Total Dapagliflozin IR | 100 | 300 |
| Total Core Bilayer |  | 1750 |

Example 7

Bilayer tablets containing reduced mass metformin (1000 mgs) extended release formulation and dapagliflozin (S) PGS (5.00 mgs) immediate release formulation were prepared as described below.

|  | % w/w | amount (mg) |
|---|---|---|
| First Layer | | |
| Metformin HCl | 76.62 | 1000 |
| Sodium Carboxymethyl Cellulose | 3.84 | 50.01 |
| Purified water or water for injection | — | q.s.[a] |
| Hydroxypropyl Methylcellulose 2208 | 18.01[b] | 235 |
| Silicon Dioxide | 1.00[c] | 13 |
| Magnesium Stearate | 0.53 | 7 |
| Total Metformin XR | 100 | 1305 |
| Second Layer | | |
| Dapagliflozin | 1.67 | 5 |
| Lactose Anhydrous | 16 | 48 |
| Microcrystalline Cellulose 302 | 75.83 | 227.5 |
| Crospovidone | 4 | 12 |
| Silicon Dioxide | 1.5 | 4.5 |
| Magnesium Stearate | 1 | 3 |
| Total Dapagliflozin IR | 100 | 300 |
| Total Core Bilayer |  | 1605 |
| Film Coat | | |
| Opadry ® II (2.5% weight gain) |  | 40.13 |
| Total Film Coated Tablet |  | 1645.13 |

[a] refers to the quantity sufficient to make the granulation composition 100% w/w
[b] The range is 15%-27%
[c] The range is 0.75%-1.25%

Metformin HCl, 0.5% magnesium stearate, and sodium carboxymethyl cellulose were combined and mixed into a high shear granulator for one minute. Purified water, using a nozzle, was added with stirring for one minute. The wet granulated material was passed through a mill and then dried until the moisture content was 1.0% or less. The dried material containing metformin HCl, 0.5% magnesium stearate, and sodium carboxymethyl cellulose was passed through a mill and discharge into polyethylene-lined drums to provide milled metformin 1 g bulk granulation.

Metformin (milled 1 g bulk granulation), hydroxypropyl methylcellulose 2208 USP (100,000 centipoise) (methocel K100M Premium), and silicon dioxide were added to a bin blender and mixed for 120 revolutions. Magnesium stearate was added, and after 60 revolutions, the material was discharge into polyethylene-lined drums to provide reduced mass metformin extended release 1 g bulk granulation.

The dapagliflozin (S) PGS granulation and the bilayer compression procedures were conducted as described in Example 4.

Example 8

Bilayer tablets containing a reduced mass metformin (1000 mgs) extended release formulation and dapagliflozin (S) PGS (2.5 mgs) immediate release formulation were prepared in a similar manner as described in Example 7.

|  | % w/w | amount (mg) |
|---|---|---|
| First Layer | | |
| Metformin HCl | 76.62 | 1000 |
| Sodium Carboxymethyl Cellulose | 3.84 | 50.01 |
| Purified water or water for injection | — | q.s.[a] |
| Hydroxypropyl Methylcellulose 2208 | 18.01[b] | 235 |
| Silicon Dioxide | 1.00[c] | 13 |
| Magnesium Stearate | 0.53 | 7 |
| Total Metformin XR | 100 | 1305 |
| Second Layer | | |
| Dapagliflozin | 0.83 | 2.50 |
| Lactose Anhydrous | 16.00 | 48.00 |
| Microcrystalline Cellulose 302 | 76.67 | 230.00 |
| Crospovidone | 4.00 | 12.00 |
| Silicon Dioxide | 1.50 | 4.50 |
| Magnesium Stearate | 1.00 | 3.00 |
| Total Dapagliflozin IR | 100 | 300 |
| Total Core Bilayer |  | 1605 |

Example 9

Bilayer tablets containing a reduced mass metformin (1000 mgs) extended release formulation and dapagliflozin (S) PGS (10.00 mgs) immediate release formulation were prepared in a similar manner as described in Example 7.

|  | % w/w | amount (mg) |
|---|---|---|
| First Layer | | |
| Metformin HCl | 76.62 | 1000 |
| Sodium Carboxymethyl Cellulose | 3.84 | 50.01 |
| Purified water or water for injection | — | q.s.[a] |
| Hydroxypropyl Methylcellulose 2208 | 18.01[b] | 235 |
| Silicon Dioxide | 1.00[c] | 13 |
| Magnesium Stearate | 0.53 | 7 |
| Total Metformin XR | 100 | 1305 |
| Second Layer | | |
| Dapagliflozin | 0.83 | 2.50 |
| Lactose Anhydrous | 16.00 | 48.00 |

-continued

| | % w/w | amount (mg) |
|---|---|---|
| Microcrystalline Cellulose 302 | 76.67 | 230.00 |
| Crospovidone | 4.00 | 12.00 |
| Silicon Dioxide | 1.50 | 4.50 |
| Magnesium Stearate | 1.00 | 3.00 |
| Total Dapagliflozin IR | 100 | 300 |
| Total Core Bilayer | | 1605 |

Other SGLT2 inhibitor IR formulations, described in Table 2, can be used to prepare bilayer tablets of the present invention. The Table 2 formulations are compatible with the metformin XR formulations or reduced mass metformin XR formulations described herein. The bilayer tablets prepared from the SGLT2 inhibitor IR formulations of Table 2 reduced or eliminated cracking, separation, and/or cross-contamination with the metformin XR layer and with the reduced mass metformin XR layer.

TABLE 2

| | % w/w | % w/w | % w/w | % w/w | % w/w |
|---|---|---|---|---|---|
| Dapagliflozin (S) PGS | 1.66 | 1.66 | 1.66 | 1.66 | 1.66 |
| Microcrystalline Cellulose 302 | 59.83 | 63.83 | 56.83 | 65.83 | 60.83 |
| Lactose Anhydrous | 16.00 | 16.00 | 16.00 | 16.00 | 16.00 |
| Pregelatinized Starch | 16.00 | 13.00 | 19.00 | — | — |
| Hydroxypropyl Cellulose EXF | — | — | — | 10.00 | — |
| Mannitol | — | — | — | — | 15.00 |
| Crospovidone | 4.00 | 4.00 | 4.00 | 4.00 | 4.00 |
| Silicon Dioxide | 1.50 | 1.50 | 1.50 | 1.50 | 1.50 |
| Magnesium stearate | 1.00 | 1.00 | 1.00 | 1.00 | 1.00 |

Example 10

Bilayer tablets containing metformin (500 mgs) extended release formulation and dapagliflozin (S) PGS (5.00 mgs) immediate release formulation were prepared in a similar manner as described in Example 13 except that silicon dioxide was not added to the metformin layer.

| Component | Function | % w/w per layer | Amount per layer (mg) |
|---|---|---|---|
| Metformin HCl XR Layer (1st Layer) | | | |
| Metformin hydrochloride | Active | 48.85 | 500.00 |
| Sodium carboxymethyl cellulose | Binder | 4.89 | 50.03 |
| Purified water or water for injection | Granulating fluid | — | q.s.[1] |
| Hydroxypropyl methylcellulose 2208 | Release modifier | 34.98 | 357.98 |
| Hydroxypropyl methylcellulose 2910 | Release modifier | 0.97 | 9.92 |
| Microcrystalline cellulose | Filler | 9.97 | 102.03 |
| Magnesium stearate | Lubricant | 0.34 | 3.53 |
| Total metformin HCl XR Layer | | 100.00 | 1023.49 |
| Dapagliflozin Layer (2nd Layer) | | | |
| Dapagliflozin | Active | 1.67 | 5.00 |
| Lactose anhydrous | Filler | 16.00 | 48.00 |
| Microcrystalline cellulose 302 | Filler | 75.83 | 227.50 |
| Crospovidone | Disintegrant | 4.00 | 12.00 |
| Silicon dioxide | Glidant | 1.50[2] | 4.50 |
| Magnesium stearate | Lubricant | 1.00 | 3.00 |
| Total dapagliflozin Layer | — | 100.00 | 300.00 |
| Total core bilayer | — | — | 1323.49 |
| Film coat component Opadry ® II (2.5% weight gain) | Coating material | — | 33.09 |
| Total film coated tablet | — | — | 1356.58 |

[1] Purified water is used only for processing and is removed during drying
[2] The range is 0.5%-1.5%

Example 11

Bilayer tablets containing metformin (500 mgs) extended release formulation and dapagliflozin (S) PGS (10.0 mgs) immediate release formulation were prepared in a similar manner as described in Example 13 except that silicon dioxide was not added to the metformin layer.

| Component | Function | % w/w per layer | Amount per layer (mg) |
|---|---|---|---|
| Metformin XR Layer (1st Layer) | | | |
| Metformin hydrochloride | Active | 48.85 | 500.00 |
| Sodium carboxymethyl cellulose | Binder | 4.89 | 50.03 |
| Purified water or water for injection | Granulating fluid | — | q.s.[1] |
| Hydroxypropyl methylcellulose 2208 | Release modifier | 34.98 | 357.98 |
| Hydroxypropyl methylcellulose 2910 | Release modifier | 0.97 | 9.92 |
| Microcrystalline cellulose | Filler | 9.97 | 102.03 |
| Magnesium stearate | Lubricant | 0.34 | 3.53 |
| Total metformin XR Layer | | 100.00 | 1023.49 |
| Dapagliflozin Layer (2nd Layer) | | | |
| Dapagliflozin | Active | 3.33 | 10.00 |
| Lactose anhydrous | Filler | 16.00 | 48.00 |
| Microcrystalline cellulose 302 | Filler | 74.17 | 222.50 |
| Crospovidone | Disintegrant | 4.00 | 12.00 |
| Silicon dioxide | Glidant | 1.50[2] | 4.50 |
| Magnesium stearate | Lubricant | 1.00 | 3.00 |
| Total dapagliflozin Layer | — | 100.00 | 300.00 |
| Total core bilayer | — | — | 1323.49 |
| Film coat component Opadry ® II (2.5% weight gain) | Coating material | — | 33.09 |
| Total film coated tablet | — | — | 1356.58 |

[1] Purified water is used only for processing and is removed during drying
[2] The range is 0.5%-1.5%

Example 12

Bilayer tablets containing metformin (500 mgs) extended release formulation and dapagliflozin (S) PGS (2.50 mgs) immediate release formulation were prepared in a similar manner as described in Example 13 except that silicon dioxide was not added to the metformin layer.

| Component | Function | % w/w per layer | Amount per layer (mg) |
|---|---|---|---|
| Metformin XR Layer (1st Layer) | | | |
| Metformin hydrochloride | Active | 48.85 | 500.00 |
| Sodium carboxymethyl cellulose | Binder | 4.89 | 50.03 |
| Purified water or water for injection | Granulating fluid | — | q.s.[1] |
| Hydroxypropyl methylcellulose 2208 | Release modifier | 34.98 | 357.98 |
| Hydroxypropyl methylcellulose 2910 | Release modifier | 0.97 | 9.92 |
| Microcrystalline cellulose | Filler | 9.97 | 102.03 |
| Magnesium stearate | Lubricant | 0.34 | 3.53 |
| Total metformin XR Layer | | 100.00 | 1023.49 |
| Dapagliflozin Layer (2nd Layer) | | | |
| Dapagliflozin | Active | 0.83 | 2.50 |
| Lactose anhydrous | Filler | 16.00 | 48.00 |
| Microcrystalline cellulose 302 | Filler | 76.67 | 230.00 |
| Crospovidone | Disintegrant | 4.00 | 12.00 |
| Silicon dioxide | Glidant | 1.50[2] | 4.50 |
| Magnesium stearate | Lubricant | 1.00 | 3.00 |
| Total dapagliflozin Layer | — | 100.00 | 300.00 |
| Total core bilayer | — | — | 1323.49 |
| Film coat component Opadry® II (2.5% weight gain) | Coating material | — | 33.09 |
| Total film coated tablet | — | — | 1356.58 |

[1] Purified water is used only for processing and is removed during drying
[2] The range is 0.5%-1.5%

Example 13

Bilayer tablets containing metformin (500 mgs) extended release formulation and dapagliflozin (S) PGS (5.0 mgs) immediate release formulation were prepared as described below.

| Component | Function | % w/w per layer | Amount per layer (mg) |
|---|---|---|---|
| Metformin XR Layer (1st Layer) | | | |
| Metformin hydrochloride | Active | 48.37 | 500.00 |
| Sodium carboxymethyl cellulose | Binder | 4.84 | 50.03 |
| Purified water or water for injection | Granulating fluid | — | q.s.[1] |
| Hydroxypropyl methylcellulose 2208 | Release modifier | 34.63 | 357.98 |
| Hydroxypropyl methylcellulose 2910 | Release modifier | 0.96 | 9.92 |
| Microcrystalline cellulose | Filler | 9.87 | 102.03 |
| Silicon dioxide | Compression aid | 0.99 | 10.24 |
| Magnesium stearate | Lubricant | 0.34 | 3.53 |
| Total metformin XR Layer | | 100.00 | 1033.73 |
| Dapagliflozin Layer (2nd Layer) | | | |
| Dapagliflozin | Active | 1.67 | 5.00 |
| Lactose anhydrous | Filler | 16.00 | 48.00 |
| Microcrystalline cellulose 302 | Filler | 75.83 | 227.50 |
| Crospovidone | Disintegrant | 4.00 | 12.00 |
| Silicon dioxide | Glidant | 1.50[2] | 4.50 |
| Magnesium stearate | Lubricant | 1.00 | 3.00 |
| Total dapagliflozin Layer | — | 100.00 | 300.00 |
| Total core bilayer | — | — | 1333.73 |
| Film coat component Opadry® II (2.5% weight gain) | Coating material | — | 33.34 |
| Total film coated tablet | — | — | 1367.07 |

[1] Purified water is used only for processing and is removed during drying
[2] The range is 0.5%-1.5%

Metformin HCl, 0.5% magnesium stearate, and sodium carboxymethyl cellulose were combined and mixed in a high shear granulator for one minute. Purified water, using a nozzle, was added with stirring for one minute. The wet granulated material was passed through a mill and then dried until the moisture content was 1.0% or less. The dried material containing metformin HCl, 0.5% magnesium stearate, and sodium carboxymethyl cellulose was passed through a mill and discharge into polyethylene lined drums to provide milled metformin 500 mg bulk granulation.

Milled metformin 500 mg bulk granulation, hydroxypropyl methyl cellulose 2208, hydroxypropyl methyl cellulose 2910, microcrystalline cellulose and silicon dioxide were added to a bin blender and mixed for 240 revolutions. Magnesium stearate was added, and after 60 revolutions, the material was discharge into polyethylene lined drums to provide metformin extended release 500 mg bulk granulation.

The dapagliflozin (S) PGS granulation and the bilayer compression procedures were conducted in a similar manner as described in Example 4.

Example 14

Bilayer tablets containing metformin (500 mgs) extended release formulation and dapagliflozin (S) PGS (10.0 mgs) immediate release formulation were prepared in a similar manner as described in Example 13.

| Component | Function | % w/w per layer | Amount per layer (mg) |
|---|---|---|---|
| Metformin XR Layer (1st Layer) | | | |
| Metformin hydrochloride | Active | 48.37 | 500.00 |
| Sodium carboxymethyl cellulose | Binder | 4.84 | 50.03 |
| Purified water or water for injection | Granulating fluid | — | q.s.[1] |
| Hydroxypropyl methylcellulose 2208 | Release modifier | 34.63 | 357.98 |
| Hydroxypropyl methylcellulose 2910 | Release modifier | 0.96 | 9.92 |
| Microcrystalline cellulose | Filler | 9.87 | 102.03 |
| Silicon dioxide | Compression aid | 0.99 | 10.24 |
| Magnesium stearate | Lubricant | 0.34 | 3.53 |
| Total metformin XR Layer | | 100.00 | 1033.73 |
| Dapagliflozin Layer (2nd Layer) | | | |
| Dapagliflozin | Active | 3.33 | 10.00 |
| Lactose anhydrous | Filler | 16.00 | 48.00 |
| Microcrystalline cellulose 302 | Filler | 74.17 | 222.50 |
| Crospovidone | Disintegrant | 4.00 | 12.00 |
| Silicon dioxide | Glidant | 1.50[2] | 4.50 |
| Magnesium stearate | Lubricant | 1.00 | 3.00 |
| Total dapagliflozin Layer | — | 100.00 | 300.00 |
| Total core bilayer | — | — | 1333.73 |

-continued

| Component | Function | % w/w per layer | Amount per layer (mg) |
|---|---|---|---|
| Film coat component Opadry ® II (2.5% weight gain) | Coating material | — | 33.34 |
| Total film coated tablet | — | — | 1367.07 |

[1]Purified water is used only for processing and is removed during drying
[2]The range is 0.5%-1.5%

Example 15

Bilayer tablets containing metformin (500 mgs) extended release formulation and dapagliflozin (S) PGS (2.50 mgs) immediate release formulation were prepared in a similar manner as described in Example 13.

| Component | Function | % w/w per layer | Amount per layer (mg) |
|---|---|---|---|
| Metformin XR Layer (1st Layer) | | | |
| Metformin hydrochloride | Active | 48.37 | 500.00 |
| Sodium carboxymethyl cellulose | Binder | 4.84 | 50.03 |
| Purified water or water for injection | Granulating fluid | — | q.s.[1] |
| Hydroxypropyl methylcellulose 2208 | Release modifier | 34.63 | 357.98 |
| Hydroxypropyl methylcellulose 2910 | Release modifier | 0.96 | 9.92 |
| Microcrystalline cellulose | Filler | 9.87 | 102.03 |
| Silicon dioxide | Compression aid | 0.99 | 10.24 |
| Magnesium stearate | Lubricant | 0.34 | 3.53 |
| Total metformin XR Layer | | 100.00 | 1033.73 |
| Dapagliflozin Layer (2nd Layer) | | | |
| Dapagliflozin | Active | 0.83 | 2.50 |
| Lactose anhydrous | Filler | 16.00 | 48.00 |
| Microcrystalline cellulose 302 | Filler | 76.67 | 230.00 |
| Crospovidone | Disintegrant | 4.00 | 12.00 |
| Silicon dioxide | Glidant | 1.50[2] | 4.50 |
| Magnesium stearate | Lubricant | 1.00 | 3.00 |
| Total dapagliflozin Layer | — | 100.00 | 300.00 |
| Total core bilayer | — | — | 1333.73 |
| Film coat component Opadry ® II (2.5% weight gain) | Coating material | — | 33.34 |
| Total film coated tablet | — | — | 1367.07 |

[1]Purified water is used only for processing and is removed during drying
[2]The range is 0.5%-1.5%

We claim:
1. A bilayer tablet comprising:
(1) a first layer wherein the first layer is a metformin extended release formulation comprising about 50-87% metformin hydrochloride (HCl) in an amount of 1000 mg, about 1-10% sodium carboxymethyl cellulose, about 10-40% hydroxypropyl methylcellulose, about 0.1-75% magnesium stearate, and about 0-2% silicon dioxide or about 0-1.5% colloidal silicon dioxide, in which weight percents are calculated relative to the total weight of the first layer;
(2) a second layer wherein the second layer is a sodium-dependent glucose transporter (SGLT2) inhibitor formulation having a total weight in the range of about 300 mg to about 400 mg and comprising about 0.1-10% of an SGLT2 inhibitor selected from dapagliflozin, dapagliflozin (S) propylene glycol hydrate and dapagliflozin (R) propylene glycol hydrate, about 5-30% lactose anhydrous, about 40-90% microcrystalline cellulose, about 0-25% pregelatinized starch, about 0-20% hydroxypropyl cellulose, about 0-25% mannitol, about 1-10% crospovidone, about 0.1-5% silicon dioxide, and about 0.1-5% magnesium stearate, in which weight percents are calculated relative to the total weight of the second layer; and
(3) optionally a film coating that covers the first layer and the second layer,
wherein the weight ratio between the first layer and the second layer is about 4.4:1.
2. The bilayer tablet according to claim 1 wherein the SGLT2 inhibitor is dapagliflozin or dapagliflozin (S) propylene glycol hydrate.
3. The bilayer tablet according to claim 1, wherein the optional film coating comprises polyvinyl alcohol, titanium dioxide, polyethylene glycol (PEG), and talc.
4. The bilayer tablet according to claim 1 wherein
(1) the first layer comprises about 64-82% metformin hydrochloride, about 3-5% sodium carboxymethyl cellulose; about 15-30% hydroxypropyl methylcellulose; about 0.1-0.75% magnesium stearate; and about 0-2% silicon dioxide or 0-1.5% colloidal silicon dioxide;
(2) the second layer comprises about 0.5-4% dapagliflozin or dapagliflozin (S) propylene glycol hydrate; about 14-18% lactose anhydrous; about 50-80% microcrystalline cellulose; about 0-20% pregelatinized starch; about 0-20% mannitol; about 0-15% hydroxypropyl cellulose; about 2-6% crospovidone; about 0.5-2.5% silicon dioxide; and about 0.5-2% magnesium stearate; and
(3) the optional film coating comprises polyvinyl alcohol, titanium dioxide, polyethylene glycol (PEG), and talc.
5. The bilayer tablet according to claim 1 wherein
the first layer comprises about 67-71% metformin hydrochloride, about 3-5% sodium carboxymethyl cellulose, about 25-29% hydroxypropyl methylcellulose 2208, and about 0.1-0.75% magnesium stearate.
6. The bilayer tablet according to claim 5 wherein the second layer comprises:
(A) about 0.5-4% dapagliflozin or dapagliflozin (S) propylene glycol hydrate; about 14-18% lactose anhydrous; about 72-80% microcrystalline cellulose 302; about 2-6% crospovidone; about 0.5-2.5% silicon dioxide; and about 0.5-1.5% magnesium stearate;
(B) about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6% crospovidone; about 0.5-2.5% silicon dioxide; and about 0.5-1.5% magnesium stearate;
(C) about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate; or
(D) about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate.

7. The bilayer tablet according to claim 6 wherein there is a film coating and the film coating comprises polyvinyl alcohol, titanium dioxide, polyethylene glycol (PEG), and talc.

8. The bilayer tablet according to claim 1 wherein the first layer comprises about 69% metformin hydrochloride, about 3.5% sodium carboxymethyl cellulose, about 27% hydroxypropyl methylcellulose 2208, and about 0.48% magnesium stearate.

9. The bilayer tablet according to claim 8 wherein the second layer comprises:
   (A) about 0.8% dapagliflozin or dapagliflozin (S) propylene glycol hydrate; about 16% lactose anhydrous; about 77% microcrystalline cellulose 302; about 4% crospovidone; about 1.5% silicon dioxide; and about 1% magnesium stearate;
   (B) about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate;
   (C) about 3.4% dapagliflozin or dapagliflozin (S) propylene glycol hydrate; about 16% lactose anhydrous; about 74% microcrystalline cellulose 302; about 4% crospovidone; about 1.5% silicon dioxide; and about 1% magnesium stearate;
   (D) about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate;
   (E) about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate;
   (F) about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate; or
   (G) about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate.

10. The bilayer tablet according to claim 9 wherein there is a film coating and the film coating comprises polyvinyl alcohol, titanium dioxide, polyethylene glycol (PEG), and talc.

11. The bilayer tablet according to claim 1 wherein the first layer comprises about 72-82% metformin hydrochloride; about 3-5% sodium carboxymethyl cellulose; about 15-22% hydroxypropyl methylcellulose 2208; about 0.75-1.25% silicon dioxide or about 0.25-0.75% colloidal silicon dioxide; and about 0.1-0.6% magnesium stearate.

12. The bilayer tablet according to claim 11 wherein the second layer comprises:
   (A) about 0.5-4% dapagliflozin or dapagliflozin (S) propylene glycol hydrate; about 14-18% lactose anhydrous; about 72-80% microcrystalline cellulose 302; about 2-6% crospovidone; about 0.5-2.5% silicon dioxide; and about 0.5-1.5% magnesium stearate;
   (B) about 0.5-4% dapagliflozin or dapagliflozin (S) propylene glycol hydrate; about 14-18% lactose anhydrous; about 50-70% microcrystalline cellulose 302; about 10-22% pregelatinized starch; about 2-6.00% crospovidone; about 0.5-2.5% silicon dioxide; and about 0.5-1.5% magnesium stearate;
   (C) about 0.5-4% dapagliflozin or dapagliflozin (S) propylene glycol hydrate; about 14-18% lactose anhydrous; about 60-70% microcrystalline cellulose 302; about 5-15% hydroxypropyl cellulose EXF; about 2-6% crospovidone; about 0.5-2.5% silicon dioxide; and about 0.5-1.5% magnesium stearate; or
   (D) about 0.5-4% dapagliflozin or dapagliflozin (S) propylene glycol hydrate; about 14-18% lactose anhydrous; about 55-65% microcrystalline cellulose 302; about 10-20% mannitol; about 2-6% crospovidone; about 0.5-2.5% silicon dioxide; and about 0.5-1.5% magnesium stearate.

13. The bilayer tablet according to claim 12 wherein there is a film coating and the film coating comprises polyvinyl alcohol, titanium dioxide, polyethylene glycol (PEG), and talc.

14. The bilayer tablet according to claim 1 wherein the first layer comprises about 76.6% metformin hydrochloride; about 3.84% sodium carboxymethyl cellulose; about 18% hydroxypropyl methylcellulose 2208; about 0.75-1.25% silicon dioxide or about 0.25-0.75% colloidal silicon dioxide; and about 0.53% magnesium stearate.

15. The bilayer tablet according to claim 14 wherein the second layer comprises:
   (A) about 0.8% dapagliflozin or dapagliflozin (S) propylene glycol hydrate; about 16% lactose anhydrous; about 77% microcrystalline cellulose 302; about 4% crospovidone; about 1.5% silicon dioxide; and about 1% magnesium stearate;
   (B) about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate;
   (C) about 3.4% dapagliflozin or dapagliflozin (S) propylene glycol hydrate, about 16% lactose anhydrous; about 74% microcrystalline cellulose 302; about 4% crospovidone; about 1.5% silicon dioxide; and about 1% magnesium stearate;
   (D) about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate;
   (E) about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate;
   (F) about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate; or
   (G) about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate.

16. The bilayer tablet according to claim 15 wherein there is a film coating and the film coating comprises polyvinyl alcohol, titanium dioxide, polyethylene glycol (PEG), and talc.

17. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 1.

18. The method according to claim 17 wherein the disorder is type II diabetes and the mammal is a human.

19. A method of treating type II diabetes in a mammal comprising administering to the mammal in need of such treatment a bilayer tablet according to claim 4.

20. A method of treating type II diabetes in a mammal comprising administering to the mammal in need of such treatment a bilayer tablet according to claim 6.

21. The method according to claim 18 wherein
   (1) the first layer comprises about 69% metformin hydrochloride; about 3.5% sodium carboxymethyl cellulose; about 27% hydroxypropyl methylcellulose 2208; and about 0.49% magnesium stearate;
   (2) the second layer and comprises
      (A) about 0.8% dapagliflozin or dapagliflozin (S) propylene glycol hydrate; about 16% lactose anhydrous; about 77% microcrystalline cellulose 302; about 4% crospovidone; about 1.5% silicon dioxide; and about 1% magnesium stearate;
      (B) about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate;
      (C) about 3.4% dapagliflozin or dapagliflozin (S) propylene glycol hydrate; about 16% lactose anhydrous; about 74% microcrystalline cellulose 302; about 4% crospovidone; about 1.5% silicon dioxide; and about 1% magnesium stearate;
      (D) about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate;
      (E) about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate;
      (F) about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate; or
      (G) about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate; and
   (3) there is a coating and the coating comprises polyvinyl alcohol, titanium dioxide, polyethylene glycol (PEG), and talc.

22. The method according to claim 18 wherein
   (1) the first layer comprises about 76.6% metformin hydrochloride, about 3.84% sodium carboxymethyl cellulose, about 18% hydroxypropyl methylcellulose 2208, about 0.75-1.25% silicon dioxide or about 0.25-0.75% colloidal silicon dioxide, and about 0.53% magnesium stearate;
   (2) the second layer comprises
      (A) about 0.8% dapagliflozin or dapagliflozin (S) propylene glycol hydrate; about 16% lactose anhydrous; about 76.6% microcrystalline cellulose 302; about 4% crospovidone; about 1.5% silicon dioxide; and about 1% magnesium stearate;
      (B) about 1.7% dapagliflozin or dapagliflozin (S) propylene glycol hydrate; about 16% lactose anhydrous; about 76% microcrystalline cellulose 302; about 4% crospovidone; about 1.5% silicon dioxide; and about 1% magnesium stearate;
      (C) about 3.4% dapagliflozin or dapagliflozin (S) propylene glycol hydrate; about 16% lactose anhydrous; about 74% microcrystalline cellulose 302; about 4% crospovidone; about 1.5% silicon dioxide; and about 1% magnesium stearate;
      (D) about 1.7% dapagliflozin or dapagliflozin (S) propylene glycol hydrate; about 16% lactose anhydrous; about 64% microcrystalline cellulose 302; about 13% pregelatinized starch; about 4% crospovidone; about 1.5% silicon dioxide; and about 1% magnesium stearate;
      (E) about 1.7% dapagliflozin or dapagliflozin (S) propylene glycol hydrate; about 16% lactose anhydrous; about 57% microcrystalline cellulose 302; about 19% pregelatinized starch; about 4% crospovidone; about 1.5% silicon dioxide; and about 1% magnesium stearate;
      (F) about 1.7% dapagliflozin or dapagliflozin (S) propylene glycol hydrate; about 16% lactose anhydrous; about 66% microcrystalline cellulose 302; about 10% hydroxypropyl cellulose EXF; about 4% crospovidone; about 1.5% silicon dioxide; and about 1% magnesium stearate; or
      (G) about 1.7% dapagliflozin or dapagliflozin (S) propylene glycol hydrate; about 16% lactose anhydrous; about 61% microcrystalline cellulose 302; about 15% mannitol; about 4% crospovidone; about 1.5% silicon dioxide; and about 1% magnesium stearate; and (3) there is a coating and the coating comprises polyvinyl alcohol, titanium dioxide, polyethylene glycol (PEG), and talc.

23. A pharmaceutical combination that comprises a bilayer tablet according to claim 1 and an anti-diabetic, wherein the anti-diabetic is a sulfonylurea, thiazolidinedione, alpha glucosidase inhibitor, meglitinide, glucagon-like peptide (GLP) agonist, insulin, amylin agonist, fructose 1,6-bis phosphatase inhibitor, insulin secretagogue, insulin sensitizer, glucokinase activator, glucocorticoid antagonist, AMP kinase activator, modulator of the incretin pathway, incretin secretagogue, incretin mimic, incretin potentiator, bile acid sequestrant or bile acid receptor agonist, TGR5 agonist, dopamine receptor agonist, aldose reductase inhibitor, PPARγ agonist, PPARα agonist, PPARδ antagonist or agonist, PPARα/γ dual agonist, 11-β-HSD-1 inhibitor, dipeptidyl peptidase IV (DPP4) inhibitor other than saxagliptin, SGLT2 inhibitor other than dapagliflozin, glucagon-like peptide-1 (GLP-1), GLP-1 agonist, or PTP-1B inhibitor.

24. A pharmaceutical combination that comprises a bilayer tablet according to claim 1 and a weight loss agent, wherein the weight loss agent is sibutrimine, a CB1 antagonist, a 5HT2C agonist, a MCHR1 antagonist, Orlistat, a thyromimetic, an amylin mimetic, or a ghrelin antagonist.

25. The bilayer tablet according to claim 1, further comprising a first coating that coats the bilayer tablet core and optionally comprises saxagliptin or a pharmaceutically acceptable salt thereof; a second coating that coats the first coating and optionally comprises saxagliptin or a pharmaceutically acceptable salt thereof; and optionally a third coating that coats the second coating; wherein at least one of the first coating and the second coating comprises saxagliptin or a pharmaceutically acceptable salt thereof.

26. The bilayer tablet according to claim 1 wherein the SGLT2 inhibitor is dapagliflozin (S) propylene glycol hydrate.

27. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 2.

28. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 3.

29. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 4.

30. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 5.

31. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 6.

32. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 8.

33. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 9.

34. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 11.

35. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 12.

36. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 14.

37. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 15.

38. A method of treating a disorder or disease selected from diabetes, impaired glucose tolerance, insulin resistance, hyperglycemia and hyperinsulinemia in a mammal comprising administering to the mammal in need of such treatment a bilayer tablet according to claim 25.

\* \* \* \* \*